(12) United States Patent
Stubbs et al.

(10) Patent No.: US 10,810,907 B2
(45) Date of Patent: Oct. 20, 2020

(54) MEDICAL TRAINING AND PERFORMANCE ASSESSMENT INSTRUMENTS, METHODS, AND SYSTEMS

(71) Applicants: NATIONAL BOARD OF MEDICAL EXAMINERS, Philadelphia, PA (US); EDUCATIONAL COMMISSION FOR FOREIGN MEDICAL GRADUATES, Philadelphia, PA (US)

(72) Inventors: Jack Stubbs, Orlando, FL (US); Fluvio Lobo, Orlando, FL (US); Kristin Stubbs, Orlando, FL (US); Kim Leblanc, Philadelphia, PA (US)

(73) Assignees: National Board of Medical Examiners, Philadelphia, PA (US); Educational Commission for Foreign Medical Graduates, Philadelphia, PA (US)

(*) Notice: Subject to any disclaimer, the term of this patent is extended or adjusted under 35 U.S.C. 154(b) by 236 days.

(21) Appl. No.: 15/846,438

(22) Filed: Dec. 19, 2017

(65) Prior Publication Data
US 2018/0174488 A1    Jun. 21, 2018

Related U.S. Application Data

(60) Provisional application No. 62/435,973, filed on Dec. 19, 2016.

(51) Int. Cl.
| G09B 23/28 | (2006.01) |
| A61B 5/16 | (2006.01) |
| G06Q 10/10 | (2012.01) |

(52) U.S. Cl.
CPC .............. *G09B 23/28* (2013.01); *A61B 5/16* (2013.01); *G06Q 10/10* (2013.01)

(58) Field of Classification Search
CPC .... G09B 23/23; G09B 23/285; G09B 23/286; G09B 23/288; G09B 23/30; G09B 23/303; A61B 5/16; G06Q 10/10
See application file for complete search history.

(56) References Cited

U.S. PATENT DOCUMENTS

| 5,766,016 A | 6/1998 | Sinclair et al. |
| 5,769,640 A | 6/1998 | Jacobus et al. |

(Continued)

FOREIGN PATENT DOCUMENTS

| WO | 9824083 A1 | 6/1998 |
| WO | 9917265 A1 | 4/1999 |

(Continued)

OTHER PUBLICATIONS

International Search Report and Written Opinion for International Application No. PCT/US2017/067214, dated Mar. 8, 2018—16 pages.

(Continued)

*Primary Examiner* — Timothy A Musselman
(74) *Attorney, Agent, or Firm* — RatnerPrestia

(57) ABSTRACT

Medical training and performance assessment instruments, methods, and systems are disclosed. Training and/or assessment systems may include an augmented medical instrument for use by a student to examine a patient. A system in accordance with one aspect of the invention includes a first augmented medical instrument configured to sense a first physical parameter during examination of a subject and produce a first examination data and a second augmented medical instrument configured to sense a second physical parameter during examination of the subject and produce a second examination data. The system is configured to generate at least one simulated physical parameter based on the first examination data and present the at least one simulated (Continued)

physical parameter to the student on the second augmented medical instrument.

18 Claims, 20 Drawing Sheets

(56) References Cited

U.S. PATENT DOCUMENTS

| | | |
|---|---|---|
| 5,771,181 A | 6/1998 | Moore et al. |
| 5,882,206 A | 3/1999 | Gillio |
| 6,126,450 A | 10/2000 | Mukai et al. |
| 6,267,599 B1 | 7/2001 | Bailey |
| 6,336,047 B1 | 1/2002 | Thu et al. |
| 6,336,812 B1 | 1/2002 | Cooper et al. |
| 6,375,471 B1 | 4/2002 | Wendlandt et al. |
| 6,398,557 B1 | 6/2002 | Hoballah |
| 6,428,323 B1 | 8/2002 | Pugh |
| 6,517,354 B1 | 2/2003 | Levy |
| 6,535,714 B2 | 3/2003 | Melker et al. |
| 6,544,041 B1 | 4/2003 | Damadian |
| 6,638,073 B1 | 10/2003 | Kazimirov et al. |
| 6,654,000 B2 | 11/2003 | Rosenberg |
| 6,863,536 B1 | 3/2005 | Fisher et al. |
| 6,918,771 B2 | 7/2005 | Arington et al. |
| 6,926,531 B2 | 8/2005 | Wallaker |
| 6,969,259 B2 | 11/2005 | Pastrick et al. |
| 6,991,464 B2 | 1/2006 | Liebert |
| 7,021,940 B2 | 4/2006 | Morris et al. |
| 7,156,664 B2 | 1/2007 | Wallaker |
| 7,215,326 B2 | 5/2007 | Rosenberg |
| 7,223,103 B2 | 5/2007 | Cantrell et al. |
| 7,249,952 B2 | 7/2007 | Ranta et al. |
| 7,261,565 B2 | 8/2007 | Chosack et al. |
| 7,316,568 B2 | 1/2008 | Gordon et al. |
| 7,347,472 B2 | 3/2008 | Pellegrin, Jr. |
| 7,427,200 B2 | 9/2008 | Noble et al. |
| 7,510,398 B1 | 3/2009 | Thornton |
| 7,520,749 B2 | 4/2009 | Ohlsson |
| 7,594,815 B2 | 9/2009 | Toly |
| 7,632,100 B2 | 12/2009 | Allen et al. |
| 7,645,141 B2 | 1/2010 | Lecat |
| 7,651,332 B2 | 1/2010 | Dupuis et al. |
| 7,715,913 B1 | 5/2010 | Froman et al. |
| 7,773,785 B2 | 8/2010 | Murphy et al. |
| 7,798,815 B2 | 9/2010 | Ramphal et al. |
| 7,862,340 B2 | 1/2011 | Chen et al. |
| 7,866,983 B2 | 1/2011 | Hemphill et al. |
| 7,878,811 B2 | 2/2011 | Earle |
| 7,931,563 B2 | 4/2011 | Shaw et al. |
| 7,959,443 B1 | 6/2011 | Frembgen et al. |
| 7,997,903 B2 | 8/2011 | Hasson et al. |
| 7,997,904 B2 | 8/2011 | Deering |
| 8,007,281 B2 | 8/2011 | Toly |
| 8,007,282 B2 | 8/2011 | Gregorio et al. |
| 8,034,006 B2 | 10/2011 | Celik-Butler et al. |
| 8,062,038 B2 | 11/2011 | Hendrikson et al. |
| 8,083,524 B2 | 12/2011 | Grund-Pedersen |
| 8,105,089 B2 | 1/2012 | Hudson |
| 8,108,190 B2 | 1/2012 | Riener et al. |
| 8,113,844 B2 | 2/2012 | Huang et al. |
| 8,113,846 B2 | 2/2012 | Wallaker et al. |
| 8,157,567 B2 | 4/2012 | Chen |
| 8,197,259 B2 | 6/2012 | Allen et al. |
| 8,241,042 B2 | 8/2012 | Rosenthal et al. |
| 8,251,703 B2 | 8/2012 | Zamierowski et al. |
| 8,287,283 B2 | 10/2012 | Lecat |
| 8,297,982 B2 | 10/2012 | Park et al. |
| 8,308,486 B2 | 11/2012 | Kokora et al. |
| 8,323,031 B2 | 12/2012 | Lecat |
| 8,323,032 B2 | 12/2012 | Deering |
| 8,364,455 B2 | 1/2013 | Blomberg et al. |
| 8,376,753 B2 | 2/2013 | Riener et al. |
| 8,382,485 B2 | 2/2013 | Bardsley et al. |
| 8,388,348 B2 | 3/2013 | Blitz et al. |
| 8,388,349 B2 | 3/2013 | Lund et al. |
| 8,388,351 B2 | 3/2013 | Cuervo et al. |
| 8,393,905 B2 | 3/2013 | Kozmenko et al. |
| 8,408,919 B2 | 4/2013 | Nauroy et al. |
| 8,428,326 B2 | 4/2013 | Falk et al. |
| 8,439,688 B2 | 5/2013 | Wilkins |
| 8,469,713 B2 | 6/2013 | Kron et al. |
| 8,480,403 B2 | 7/2013 | Jarrell et al. |
| 8,480,404 B2 | 7/2013 | Savitsky |
| 8,480,406 B2 | 7/2013 | Alexander et al. |
| 8,485,829 B2 | 7/2013 | Cusano et al. |
| 8,491,307 B2 | 7/2013 | Grund-Pederson et al. |
| 8,500,451 B2 | 8/2013 | Bronstein et al. |
| 8,500,452 B2 | 8/2013 | Trotta et al. |
| 8,550,821 B2 | 10/2013 | Illana Alejandro et al. |
| 8,556,635 B2 | 10/2013 | Toly |
| 8,591,236 B2 | 11/2013 | Vecerina et al. |
| 8,600,551 B2 | 12/2013 | Itkowitz et al. |
| 8,616,894 B2 | 12/2013 | Ehrhardt et al. |
| 8,632,343 B2 | 1/2014 | Blackburn |
| 8,639,485 B2 | 1/2014 | Connacher et al. |
| 8,647,124 B2 | 2/2014 | Bardsley et al. |
| 8,690,581 B2 | 4/2014 | Ruf et al. |
| 8,696,363 B2 | 4/2014 | Gray et al. |
| 8,696,572 B2 | 4/2014 | Canfield |
| 8,740,624 B2 | 6/2014 | Eggert et al. |
| 8,753,296 B2 | 6/2014 | Einav et al. |
| 8,755,736 B2 | 6/2014 | Huang |
| 8,764,450 B2 | 7/2014 | Pugh |
| 8,784,111 B2 | 7/2014 | Feygin et al. |
| 8,786,613 B2 | 7/2014 | Millman |
| 8,794,973 B2 | 8/2014 | Darois et al. |
| 8,801,438 B2 | 8/2014 | Sakezles |
| 8,812,431 B2 | 8/2014 | Voigt et al. |
| 8,814,573 B2 | 8/2014 | Nguyen |
| 8,827,708 B2 | 9/2014 | Christensen et al. |
| 8,827,719 B2 | 9/2014 | Kellermann et al. |
| 8,827,720 B1 | 9/2014 | Lazarus et al. |
| 8,831,924 B2 | 9/2014 | Avisar |
| 8,834,171 B2 | 9/2014 | Gloeggler et al. |
| 8,858,233 B2 | 10/2014 | Speiser et al. |
| 8,882,511 B2 | 11/2014 | McKenzie et al. |
| 8,888,495 B2 | 11/2014 | Johnson et al. |
| 8,899,989 B2 | 12/2014 | Mourton |
| 8,911,238 B2 | 12/2014 | Forsythe |
| 8,917,916 B2 | 12/2014 | Martin et al. |
| 8,924,334 B2 | 12/2014 | Lacey et al. |
| 8,926,334 B2 | 1/2015 | Park et al. |
| 8,934,636 B2 | 1/2015 | Ferzli et al. |
| 8,956,165 B2 | 2/2015 | Kurenov et al. |
| 8,961,188 B1 | 2/2015 | Singh et al. |
| 8,961,190 B2 | 2/2015 | Hart et al. |
| 9,022,788 B2 | 5/2015 | Stahler |
| 9,028,258 B2 | 5/2015 | Burdea |
| 9,053,641 B2 | 6/2015 | Samosky |
| 9,064,427 B2 | 6/2015 | Shibui et al. |
| 9,064,428 B2 | 6/2015 | Lecat |
| 9,070,306 B2 | 6/2015 | Rappel et al. |
| 9,082,319 B2 | 7/2015 | Shimada et al. |
| 9,087,456 B2 | 7/2015 | Allen et al. |
| 9,092,995 B2 | 7/2015 | Pastrick et al. |
| 9,092,996 B2 | 7/2015 | Meglan et al. |
| 9,104,791 B2 | 8/2015 | Cohen et al. |
| 9,105,200 B2 | 8/2015 | Chen et al. |
| 9,111,026 B1 | 8/2015 | Fernandez |
| 9,123,261 B2 | 9/2015 | Lowe |
| 9,129,055 B2 | 9/2015 | Mordaunt et al. |
| 9,142,144 B2 | 9/2015 | Meglan et al. |
| 9,142,145 B2 | 9/2015 | Tuchschmid et al. |
| 9,153,146 B2 | 10/2015 | Hyltander et al. |
| 9,183,763 B2 | 11/2015 | Carson et al. |
| 9,208,696 B2 | 12/2015 | Rodriguez et al. |
| 9,214,095 B2 | 12/2015 | Kubota et al. |
| 9,214,096 B2 | 12/2015 | Stahler et al. |
| 9,218,752 B2 | 12/2015 | Gillies et al. |
| 9,230,452 B2 | 1/2016 | Hyltander et al. |
| 9,240,130 B2 | 1/2016 | Carvajal et al. |
| 9,251,721 B2 | 2/2016 | Lampotang et al. |
| 9,257,055 B2 | 2/2016 | Endo et al. |
| 9,262,943 B2 | 2/2016 | Clash |

(56) References Cited

U.S. PATENT DOCUMENTS

| | | |
|---|---|---|
| 9,269,275 B2 | 2/2016 | Bell et al. |
| 9,280,916 B2 | 3/2016 | Zamierowski et al. |
| 9,286,809 B2 | 3/2016 | Yang et al. |
| 9,293,064 B2 | 3/2016 | Crary et al. |
| 9,318,032 B2 | 4/2016 | Samosky et al. |
| 9,323,896 B2 | 4/2016 | Fält et al. |
| 9,330,502 B2 | 5/2016 | Tuchschmid et al. |
| 9,336,691 B2 | 5/2016 | Cunningham et al. |
| 9,342,996 B2 | 5/2016 | King |
| 9,355,574 B2 | 5/2016 | Jian et al. |
| 9,361,808 B1 | 6/2016 | Caron |
| 9,361,809 B1 | 6/2016 | Caron |
| 9,373,269 B2 | 6/2016 | Bergman et al. |
| 9,378,659 B2 | 6/2016 | Eggert et al. |
| 9,390,626 B1 | 7/2016 | Horowitz et al. |
| 9,396,669 B2 | 7/2016 | Karkanias et al. |
| 9,406,244 B2 | 8/2016 | Eggert et al. |
| 9,418,574 B2 | 8/2016 | Park et al. |
| 9,424,656 B2 | 8/2016 | Luo et al. |
| 9,424,761 B2 | 8/2016 | Tuchschmid et al. |
| 9,430,955 B2 | 8/2016 | Daullary |
| 9,437,117 B2 | 9/2016 | Carvajal et al. |
| 9,443,445 B2 | 9/2016 | Laurusonis et al. |
| 9,443,446 B2 | 9/2016 | Rios et al. |
| 9,460,637 B2 | 10/2016 | Nakaguchi et al. |
| 9,460,638 B2 | 10/2016 | Baker et al. |
| 9,472,121 B2 | 10/2016 | Pravong et al. |
| 9,472,122 B2 | 10/2016 | Sakezles |
| 9,489,869 B2 | 11/2016 | Riojas et al. |
| 9,489,870 B2 | 11/2016 | Rodriguez et al. |
| 9,495,885 B2 | 11/2016 | Miller |
| 9,501,953 B2 | 11/2016 | Carvajal et al. |
| 9,501,955 B2 | 11/2016 | Chosack et al. |
| 9,542,853 B1 | 1/2017 | Bergeron |
| 9,542,861 B2 | 1/2017 | Day et al. |
| 9,542,862 B2 | 1/2017 | Shim et al. |
| 9,548,003 B2 | 1/2017 | Forte et al. |
| 9,552,746 B2 | 1/2017 | Caron et al. |
| 9,563,266 B2 | 2/2017 | Banerjee et al. |
| 9,569,978 B2 | 2/2017 | Hussam |
| 9,569,985 B2 | 2/2017 | Alkhatib et al. |
| 9,576,106 B2 | 2/2017 | Ahmad |
| 9,576,503 B2 | 2/2017 | Stephanian |
| 9,585,603 B2 | 3/2017 | Centen |
| 9,589,483 B2 | 3/2017 | Buckman |
| 9,595,207 B2 | 3/2017 | Kesavadas et al. |
| 9,595,208 B2 | 3/2017 | Ottensmeyer et al. |
| 9,601,030 B2 | 3/2017 | Ratcliffe et al. |
| 9,601,031 B1 | 3/2017 | Gutierrez Morales |
| 9,607,528 B2 | 3/2017 | Meglan et al. |
| 9,614,745 B2 | 4/2017 | Mathur et al. |
| 9,626,805 B2 | 4/2017 | Lampotang et al. |
| 9,633,577 B2 | 4/2017 | Constantine, III |
| 9,639,661 B2 | 5/2017 | Salkowski |
| 9,640,089 B2 | 5/2017 | Miller et al. |
| 9,664,538 B2 | 5/2017 | Hoyt et al. |
| 9,679,500 B2 | 6/2017 | Welch et al. |
| 9,679,501 B2 | 6/2017 | Sakezles |
| 9,694,155 B2 | 7/2017 | Panova et al. |
| 9,694,539 B2 | 7/2017 | Van Lierde et al. |
| 9,697,749 B2 | 7/2017 | Eggert et al. |
| 9,697,750 B2 | 7/2017 | Rodriguez et al. |
| 9,700,292 B2 | 7/2017 | Nawana et al. |
| 9,711,066 B2 | 7/2017 | Van Dinther |
| 9,711,067 B2 | 7/2017 | Feins et al. |
| 9,715,839 B2 | 7/2017 | Pybus et al. |
| 9,721,482 B2 | 8/2017 | Lowe et al. |
| 9,721,483 B2 | 8/2017 | Cowperthwait et al. |
| 2002/0076679 A1 | 6/2002 | Aman |
| 2003/0061070 A1 | 3/2003 | Kelly et al. |
| 2004/0064298 A1 | 4/2004 | Levine |
| 2004/0175684 A1 | 9/2004 | Kaasa et al. |
| 2004/0224294 A1 | 11/2004 | Heininger et al. |
| 2004/0234933 A1 | 11/2004 | Dawson et al. |
| 2005/0020409 A1 | 1/2005 | Hayamizu et al. |
| 2005/0048455 A1 | 3/2005 | Hayamizu et al. |
| 2005/0142525 A1 | 6/2005 | Cotin et al. |
| 2005/0255434 A1 | 11/2005 | Lok et al. |
| 2006/0040245 A1 | 2/2006 | Airola et al. |
| 2006/0286524 A1 | 12/2006 | Boyers et al. |
| 2007/0166681 A1 | 7/2007 | Hemphill et al. |
| 2007/0166682 A1 | 7/2007 | Yarin et al. |
| 2007/0178430 A1 | 8/2007 | Lecat |
| 2007/0207448 A1 | 9/2007 | Glaser et al. |
| 2008/0014566 A1 | 1/2008 | Chapman et al. |
| 2008/0085499 A1 | 4/2008 | Horvath |
| 2008/0118902 A1 | 5/2008 | Matsumura |
| 2008/0176198 A1 | 7/2008 | Ansari et al. |
| 2009/0017430 A1 | 1/2009 | Muller-Daniels et al. |
| 2009/0098522 A1 | 4/2009 | Marcovitz |
| 2009/0112538 A1 | 4/2009 | Anderson et al. |
| 2009/0130642 A1 | 5/2009 | Tada et al. |
| 2009/0162820 A1 | 6/2009 | Tada et al. |
| 2009/0177452 A1 | 7/2009 | Ullrich et al. |
| 2009/0202972 A1 | 8/2009 | Adhami et al. |
| 2009/0253109 A1 | 10/2009 | Anvari et al. |
| 2009/0263775 A1 | 10/2009 | Ullrich |
| 2009/0305213 A1 | 12/2009 | Burgkart et al. |
| 2009/0325135 A1 | 12/2009 | Huang et al. |
| 2010/0003657 A1 | 1/2010 | Shibui et al. |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0178644 A1 | 7/2010 | Meglan et al. |
| 2010/0248200 A1 | 9/2010 | Ladak et al. |
| 2010/0285438 A1 | 11/2010 | Kesavadas et al. |
| 2011/0014596 A1 | 1/2011 | Kurenov et al. |
| 2011/0015486 A1 | 1/2011 | Yamamoto et al. |
| 2011/0046637 A1 | 2/2011 | Patel et al. |
| 2011/0091856 A1 | 4/2011 | Ruf et al. |
| 2011/0098638 A1 | 4/2011 | Chawla et al. |
| 2011/0117530 A1 | 5/2011 | Albocher et al. |
| 2011/0144658 A1 | 6/2011 | Wenderow et al. |
| 2011/0165547 A1 | 7/2011 | Hudson |
| 2011/0170752 A1 | 7/2011 | Martin et al. |
| 2011/0207102 A1 | 8/2011 | Trotta et al. |
| 2011/0236866 A1 | 9/2011 | Psaltis et al. |
| 2011/0236868 A1 | 9/2011 | Bronstein et al. |
| 2011/0287398 A1 | 11/2011 | Blackburn |
| 2012/0064497 A1 | 3/2012 | Wu |
| 2012/0100517 A1 | 4/2012 | Bowditch et al. |
| 2012/0115117 A1 | 5/2012 | Marshall |
| 2012/0115118 A1 | 5/2012 | Marshall |
| 2012/0156665 A1 | 6/2012 | Samosky |
| 2012/0178062 A1 | 7/2012 | Flaction et al. |
| 2012/0178069 A1 | 7/2012 | McKenzie et al. |
| 2012/0189998 A1 | 7/2012 | Kruecker et al. |
| 2012/0219937 A1 | 8/2012 | Hughes et al. |
| 2012/0225413 A1 | 9/2012 | Kotranza et al. |
| 2012/0251987 A1 | 10/2012 | Huang et al. |
| 2012/0282583 A1 | 11/2012 | Thaler et al. |
| 2012/0288838 A1 | 11/2012 | Shachar et al. |
| 2013/0065211 A1 | 3/2013 | Amso et al. |
| 2013/0071826 A1 | 3/2013 | Johnson |
| 2013/0157239 A1 | 6/2013 | Russo |
| 2013/0209980 A1 | 8/2013 | Kuchenbecker et al. |
| 2013/0252219 A1 | 9/2013 | Lecat |
| 2014/0071165 A1 | 3/2014 | Tuchschmid et al. |
| 2014/0087346 A1 | 3/2014 | Breslin et al. |
| 2014/0087347 A1 | 3/2014 | Tracy et al. |
| 2014/0093852 A1 | 4/2014 | Poulsen et al. |
| 2014/0093854 A1 | 4/2014 | Poulsen et al. |
| 2014/0099617 A1 | 4/2014 | Tallman, Jr. |
| 2014/0106328 A1 | 4/2014 | Loor |
| 2014/0134587 A1 | 5/2014 | Forte et al. |
| 2014/0155910 A1 | 6/2014 | Hannaford et al. |
| 2014/0170620 A1 | 6/2014 | Savitsky et al. |
| 2014/0170621 A1 | 6/2014 | Steward, Jr. et al. |
| 2014/0180416 A1 | 6/2014 | Radojicic |
| 2014/0193789 A1 | 7/2014 | Imanaka et al. |
| 2014/0199673 A1 | 7/2014 | Jian et al. |
| 2014/0212860 A1 | 7/2014 | Bai et al. |
| 2014/0212862 A1 | 7/2014 | Rodriguez et al. |

(56) References Cited

U.S. PATENT DOCUMENTS

| | | |
|---|---|---|
| 2014/0248596 A1 | 9/2014 | Hart et al. |
| 2014/0272863 A1 | 9/2014 | Kim |
| 2014/0272873 A1 | 9/2014 | Svensson et al. |
| 2014/0287395 A1 | 9/2014 | Silvergate et al. |
| 2014/0302473 A1 | 10/2014 | Nakaguchi et al. |
| 2014/0315174 A1 | 10/2014 | Sassani et al. |
| 2014/0322688 A1 | 10/2014 | Park et al. |
| 2014/0329215 A1 | 11/2014 | Pugh |
| 2014/0329217 A1 | 11/2014 | Barsness et al. |
| 2014/0342333 A1 | 11/2014 | Knoche et al. |
| 2014/0349264 A1 | 11/2014 | Shabat et al. |
| 2014/0349266 A1 | 11/2014 | Choi |
| 2014/0356834 A1 | 12/2014 | Patrickson et al. |
| 2014/0363801 A1 | 12/2014 | Samosky et al. |
| 2014/0370475 A1 | 12/2014 | Bova et al. |
| 2015/0004583 A1 | 1/2015 | Lavigueur et al. |
| 2015/0024361 A1 | 1/2015 | Williams |
| 2015/0037773 A1 | 2/2015 | Quirarte Catano |
| 2015/0044653 A1 | 2/2015 | Levine et al. |
| 2015/0044654 A1 | 2/2015 | Lendvay et al. |
| 2015/0056591 A1 | 2/2015 | Tepper et al. |
| 2015/0056592 A1 | 2/2015 | Cowperthwait |
| 2015/0064675 A1 | 3/2015 | Eichhorn et al. |
| 2015/0079565 A1 | 3/2015 | Miller et al. |
| 2015/0086955 A1* | 3/2015 | Poniatowski ......... G09B 23/28 434/267 |
| 2015/0086958 A1 | 3/2015 | Lewis |
| 2015/0104773 A1 | 4/2015 | Toly et al. |
| 2015/0127316 A1 | 5/2015 | Avisar |
| 2015/0132732 A1 | 5/2015 | Hart et al. |
| 2015/0140535 A1 | 5/2015 | Geri et al. |
| 2015/0147736 A1 | 5/2015 | Mathur |
| 2015/0161347 A1 | 6/2015 | Christiansen et al. |
| 2015/0170546 A1 | 6/2015 | Kirenko |
| 2015/0173715 A1 | 6/2015 | Raghavan et al. |
| 2015/0187229 A1 | 7/2015 | Wachli et al. |
| 2015/0194066 A1 | 7/2015 | Samosky et al. |
| 2015/0194074 A1 | 7/2015 | Chen et al. |
| 2015/0199920 A1 | 7/2015 | Rowbottom et al. |
| 2015/0199921 A1 | 7/2015 | Segall |
| 2015/0206457 A1 | 7/2015 | Zamierowski et al. |
| 2015/0221236 A1 | 8/2015 | Forte et al. |
| 2015/0221238 A1 | 8/2015 | Huebner |
| 2015/0235569 A1 | 8/2015 | Babiker et al. |
| 2015/0235571 A1 | 8/2015 | Alexandersson |
| 2015/0255004 A1 | 9/2015 | Manzke et al. |
| 2015/0262511 A1 | 9/2015 | Lin et al. |
| 2015/0269870 A1 | 9/2015 | McGill |
| 2015/0279237 A1 | 10/2015 | Sugiyama |
| 2015/0279238 A1 | 10/2015 | Forte et al. |
| 2015/0283342 A1 | 10/2015 | Mielcarz et al. |
| 2015/0294599 A1 | 10/2015 | Nitsche et al. |
| 2015/0302776 A1 | 10/2015 | Olmstead et al. |
| 2015/0310768 A1 | 10/2015 | Felger et al. |
| 2015/0317909 A1* | 11/2015 | Florkoski ............... G09B 23/28 434/270 |
| 2015/0325148 A1 | 11/2015 | Kim et al. |
| 2015/0347682 A1 | 12/2015 | Chen et al. |
| 2015/0348429 A1 | 12/2015 | Dalal et al. |
| 2015/0356890 A1 | 12/2015 | Siassi |
| 2015/0356891 A1 | 12/2015 | Will |
| 2015/0371558 A1 | 12/2015 | Katayama et al. |
| 2015/0371560 A1 | 12/2015 | Lowe |
| 2015/0379882 A1 | 12/2015 | Gaitán et al. |
| 2015/0379900 A1 | 12/2015 | Samosky et al. |
| 2015/0379901 A1 | 12/2015 | Welch et al. |
| 2016/0005338 A1 | 1/2016 | Melendez-Calderon et al. |
| 2016/0012349 A1 | 1/2016 | Lai et al. |
| 2016/0027319 A1 | 1/2016 | London |
| 2016/0027341 A1 | 1/2016 | Kerins |
| 2016/0027342 A1 | 1/2016 | Ben-Haim |
| 2016/0027345 A1 | 1/2016 | Carson et al. |
| 2016/0055767 A1 | 2/2016 | Tessier et al. |
| 2016/0086514 A1 | 3/2016 | Washburn et al. |
| 2016/0098935 A1 | 4/2016 | Duval-Arnould et al. |
| 2016/0098943 A1 | 4/2016 | Valeev et al. |
| 2016/0098944 A1 | 4/2016 | Lin |
| 2016/0111021 A1 | 4/2016 | Knoche et al. |
| 2016/0125765 A1 | 5/2016 | Meretei et al. |
| 2016/0133158 A1 | 5/2016 | Sui et al. |
| 2016/0148540 A1 | 5/2016 | Vozenilek et al. |
| 2016/0225290 A1 | 8/2016 | Barash et al. |
| 2016/0249989 A1 | 9/2016 | Devam et al. |
| 2016/0275819 A1 | 9/2016 | Hofstetter et al. |
| 2016/0287207 A1 | 10/2016 | Xue |
| 2016/0293053 A1 | 10/2016 | Azevedo |
| 2016/0314710 A1 | 10/2016 | Jarc et al. |
| 2016/0321956 A1 | 11/2016 | Jarc et al. |
| 2016/0328998 A1 | 11/2016 | Pedersen et al. |
| 2017/0011656 A1 | 1/2017 | Cobb |
| 2017/0046985 A1 | 2/2017 | Hendrickson et al. |
| 2017/0061831 A1 | 3/2017 | Stephanian |
| 2017/0108930 A1 | 4/2017 | Banerjee et al. |
| 2017/0140671 A1 | 5/2017 | Chui et al. |
| 2017/0154544 A1 | 6/2017 | Hussam |
| 2017/0162079 A1 | 6/2017 | Helybely |
| 2017/0169732 A1 | 6/2017 | Perone |
| 2017/0178540 A1 | 6/2017 | Rios et al. |
| 2017/0193857 A1 | 7/2017 | Shaw et al. |
| 2017/0193858 A1 | 7/2017 | Segall |
| 2017/0213473 A1 | 7/2017 | Ribeira et al. |
| 2017/0221386 A1 | 8/2017 | Lowe et al. |
| 2017/0221387 A1 | 8/2017 | Lampotang et al. |

FOREIGN PATENT DOCUMENTS

| | | |
|---|---|---|
| WO | 9942978 A1 | 8/1999 |
| WO | 0188881 A2 | 11/2001 |
| WO | 03054834 A1 | 7/2003 |
| WO | 2004015654 A1 | 2/2004 |
| WO | 2004029908 A1 | 4/2004 |
| WO | 2004029909 A1 | 4/2004 |
| WO | 2004030599 A2 | 4/2004 |
| WO | 2004077202 A2 | 9/2004 |
| WO | 2005041148 A1 | 5/2005 |
| WO | 2005083653 A1 | 9/2005 |
| WO | 2005096247 A1 | 10/2005 |
| WO | 2005122105 A2 | 12/2005 |
| WO | 2006037946 A1 | 4/2006 |
| WO | 2007068050 A1 | 6/2007 |
| WO | 2008023984 A1 | 2/2008 |
| WO | 2008122006 A1 | 10/2008 |
| WO | 2009008750 A1 | 1/2009 |
| WO | 2009009820 A1 | 1/2009 |
| WO | 2009135956 A1 | 11/2009 |
| WO | 2010043043 A2 | 4/2010 |
| WO | 2010071533 A1 | 6/2010 |
| WO | 2010097771 A2 | 9/2010 |
| WO | 2011051172 A1 | 5/2011 |
| WO | 2011107088 A1 | 9/2011 |
| WO | 2012031562 A1 | 3/2012 |
| WO | 2014132024 A1 | 9/2014 |
| WO | 2014132026 A1 | 9/2014 |
| WO | 2015042274 A1 | 3/2015 |
| WO | 2015089118 A1 | 6/2015 |
| WO | 2015102484 A1 | 7/2015 |
| WO | 2015150553 A1 | 10/2015 |
| WO | 2015198023 A1 | 12/2015 |
| WO | 2016005959 A1 | 1/2016 |
| WO | 2016026818 A1 | 2/2016 |
| WO | 2016026819 A1 | 2/2016 |
| WO | 2016026821 A1 | 2/2016 |
| WO | 2016028821 A1 | 2/2016 |
| WO | 2016081370 A1 | 5/2016 |
| WO | 2016109879 A1 | 7/2016 |
| WO | 2016118593 A1 | 7/2016 |
| WO | 2016122383 A1 | 7/2016 |
| WO | 2016154743 A1 | 10/2016 |
| WO | 2016154745 A1 | 10/2016 |
| WO | 2016182477 A1 | 11/2016 |
| WO | 2016196658 A1 | 12/2016 |
| WO | 2016207762 A1 | 12/2016 |
| WO | 2017030435 A1 | 2/2017 |
| WO | 2017048929 A1 | 3/2017 |

(56) References Cited

FOREIGN PATENT DOCUMENTS

| | | |
|---|---|---|
| WO | 2017048931 A1 | 3/2017 |
| WO | 2017074176 A1 | 5/2017 |
| WO | 2017086774 A1 | 5/2017 |
| WO | 2017098036 A1 | 6/2017 |
| WO | 2017098506 A1 | 6/2017 |
| WO | 2017106924 A1 | 6/2017 |
| WO | 2017126313 A1 | 7/2017 |
| WO | 2017127724 A1 | 7/2017 |

OTHER PUBLICATIONS

Kamphuis et al., "Augmented Reality in Medical Education?", Perspect Med. Educ., 2014, 3, pp. 300-311.

Khor et al., "Augmented and Virtual Reality in Surgery—the Digital Surgical Environment: Applications, Limitations and Legal Battles", Ann. Transl. Med., 2016, 4(23)—10 pages.

Kidane et al., "Orientation Invariant ECG-based Stethoscope Tracking for Heart Auscultation Training on Augmented Standardized Patients", Simulation: Transactions of the Society for Modeling and Simulation International, 89(12), pp. 1450-1458.

Malek et al., "Design and Development of Wireless Stethoscope with Data Logging Functions", 2013 IEEE International Conference on Control System, Computing and Engineering, IEEE, Nov. 29, 2013—41 pages.

Ricci et al., "Ophthalmoscopy Simulation: Advances in Training and Practice for Medical Students and Young Ophthalmologists", Advances in Medical Education and Practice, 2017:8—pp. 435-439.

Ting et al., "Ophthalmology Simulation for Undergraduate and Postgraduate Clinical Education", Int. J. Ophthalmol., vol. 9, No. 6, Jun. 18, 2016—pp. 920-924.

International Preliminary Report on Patentability and Written Opinion issued in International Application No. PCT/US2017/067214, dated Jun. 25, 2019, 10 pages.

\* cited by examiner

MEDICAL TRAINING AND PERFORMANCE ASSESSMENT INSTRUMENTS, METHODS, AND SYSTEMS

CROSS REFERENCE TO RELATED APPLICATIONS

This application claims priority to and benefit of U.S. Provisional Patent Application No. 62/435,973, filed Dec. 19, 2016, the entire disclosure of which is incorporated herein by reference.

FIELD OF THE INVENTION

The invention relates to training and assessment and, more particularly, to medical instruments, methods, and systems for use in training and assessment.

BACKGROUND OF THE INVENTION

Conventional medical training and performance assessment systems train students utilizing standard medical instruments such as stethoscopes, otoscopes, and ophthalmoscopes. Part of a student's training involves the examination of standardized "patients" (subjects/actors that present symptoms for examination by the students). An observer may be present to witness and assess the examination and to provide feedback to the students after the examination. Such systems are very subjective. More objective medical training and performance assessment instruments, methods, and systems would be useful. Aspects of the invention address these among others.

SUMMARY OF THE INVENTION

The invention is embodied in medical instruments, methods, and systems for training and/or assessing performance of students. Training and/or assessment systems may include an augmented medical instrument for use by a student to examine a patient. A system in accordance with one aspect of the so invention includes a first augmented medical instrument configured to sense a first physical parameter during examination of a subject and produce a first examination data and a second augmented medical instrument configured to sense a second physical parameter during examination of the subject and produce a second examination data. The system is configured to generate at least one simulated physical parameter based on the first examination data and present the at least one simulated physical parameter to the student on the second augmented medical instrument.

A method according to one aspect of the Invention includes sensing one or more physical parameters with an augmented medical instrument during examination of a subject by a student; producing an output signal with a processor, the output signal including examination data corresponding to the one or more sensed to physical parameters; and presenting at least one simulated physical parameter as content to the student.

An apparatus in accordance with one aspect of the invention includes at least one sensor configured to sense at least one physical parameter during examination of a subject by a student. The apparatus also having a processor configured to receive the at least one sensed physical parameter, produce examination data that corresponds to the at least one sensed physical parameters, present at least one of an output signal including the examination data or an output signal including augmented data.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. Also, lines without arrows connecting instruments may represent a bi-directional exchange between these instruments. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Aspects of the invention relate to medical devices, instruments, methods/processes, and systems to develop improved and enhanced metrics and features for teaching medical skills to students (e.g., trainees/examinees) and assessing those skills, e.g., for the standardized general medical clinical skills exam (United States Medical Licensing Examination; USMLE). The clinical skills portion of the USMLE is largely based on the use of standardized patients/subjects. To improve the ability to assess medical knowledge and patient care, aspects of the invention provide the student with augmented diagnostic instruments that gather objective information during examinations and/or present audio/visual media overlays (e.g., heart murmur sounds, cataract images, etc.) for the subject being examined. As used herein, the term "student" is meant to refer to individuals that are being trained and/or assessed. The term "student" is used herein to encompass individuals traditionally thought of as student (e.g., medical students) and other individuals that may be trained and/or assessed (e.g., registered nurses, doctors, etc.)

The augmented diagnostic instruments provide (or mimic) the performance and functionality of conventional diagnostic instruments, e.g., stethoscopes, blood pressure cuffs, otoscopes, ophthalmoscopes, etc. Additionally, the augmented instruments include integrated technology for generating measurements useful in training the students, e.g., by determining if the student has performed skills and steps that are required to pass an exam such as the USMLE. The measurements gained from the augmented instruments enable novel testing scenarios that provide greater objectivity than previously available.

Figure 1A:
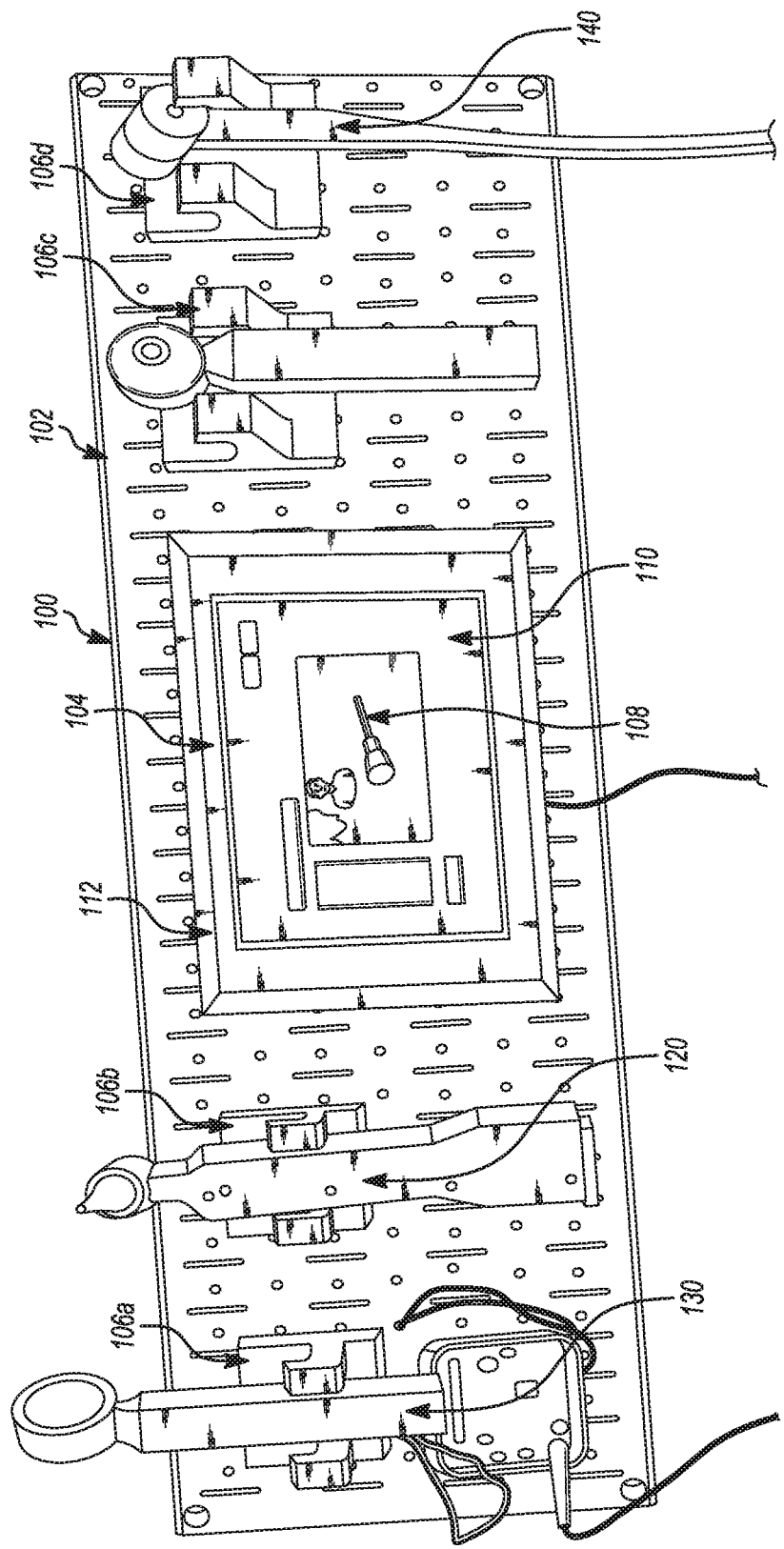
FIG. 1A is an illustration of a base system in accordance with aspects of the invention.

FIG. 1A depicts a base system 100 in accordance with aspects of the invention. The base system 100 includes an instrument module 102, control module 104, and a plurality of instrument receptacle modules 106a-d configured to receive augmented instruments. The base system 100 may also include a power module (not shown) for providing power to control module 104 and the augmented instruments. The power source may include an AC/DC converter for converting AC power from a conventional electrical outlet to DC power (e.g., 3.5/5 Volts). Also depicted in FIG. 1A are augmented instruments—including an otoscope 120, an ophthalmoscope 130, and a stethoscope 140. The base system 100 may additionally include a camera (not shown) such as a webcam for capturing images and/or remote observation during examinations.

The instrument receptacle modules 106 each include a connection base configured to receive a respective augmented instrument, a presence sensor (e.g., a proximity switch) configured to detect when an augmented instrument is placed in and/or removed from the instrument receptacle module 106, a data connection port configured for passing communication between the control module 104 and the augmented instrument when placed in the connection base, and a battery charging port configured to pass power from the power source of the base system 100 to augmented instrument to charge the augmented instrument when placed in the connection base.

The Illustrated instrument module 102 is a wall mounted instrument panel, e.g., for use in testing/examination rooms. The instrument module 102 may take other forms. The instrument panel 104 is configured to provide mechanical, electrical, and communication functionality and connections. In the illustrated embodiment, the instrument panel 102 is modular. In alternative embodiment, the instrument panel may be integrated into a single housing. The panel may be fastened to the wall as a standard Welch Allyn panel.

The control module 104 communicates with the augmented instruments and has a user interface 108 for receiving information from a user and presenting information to the user. The user interface 108 may be used to set up the control module 104 and the augmented instruments. The depicted user interface 108 is a touchscreen 110, which is supported by a housing 112 of the control module 104. The user interface 108 includes a graphical user interface for presenting information and receiving user input. The touchscreen 110 may include a camera such as a conventional webcam. A suitable touchscreen 110 is a Pi Foundation PiTFT—7" Touchscreen Display for Raspberry P available from Adafruit Industries, LLC of New York, N.Y.

In an embodiment, the base system 100 is module-based including the instrument module 102, the control module 104, and the instrument receptacle modules 106. The instrument receptacle modules 106 may power and hold augmented handle modules (described below). The base system 100 may additionally include a power supply module (not shown) that supplies regulated power (e.g., regulated voltage levels) to other modules in the base system 102 and/or the augmented instruments. In other embodiment, one or more of the modules may be combined into a single integrated unit.

The augmented instruments, which are described in further detail below, may additionally be module-based. Augmented instruments such as an otoscope and ophthalmoscope may each include a augmented handle module coupled to an otoscope module or an ophthalmoscope module, respectively. The otoscope module may include conventional otoscope optics and be configured for connection to the augmented handle module. The ophthalmoscope module may include conventional ophthalmoscope optics and/or electronics capable of streaming and recording video, and be configured for connection to the augmented handle module. The augmented handle module may acquire data (e.g., examination data) related to the use and implementation of the module to which it is attached (e.g., position, orientation, movement, distance to object, etc.) An augmented instrument such as a stethoscope may be a single construction module including electronics and acoustics for recording and processing audio signals. One or more of the modules (e.g., the augmented handle module and the stethoscope module may include transceivers for communicating with the control module 106.

Figure 1B:
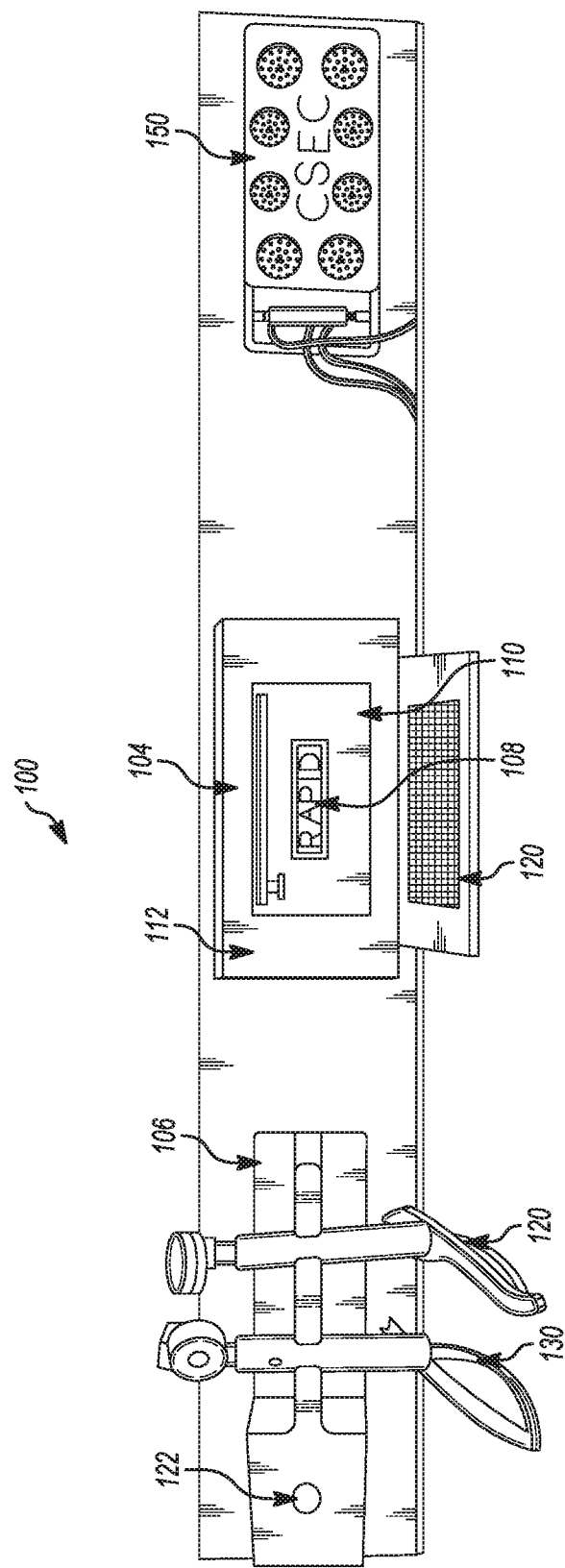
FIG. 1B is an illustration of another base system in accordance with aspects of the invention.

FIG. 1B depicts another example of base system 100 in accordance with aspects of the invention. Similar components between the base systems 100 depicted in FIGS. 1A and 1B are identified with common numbers and only differences are described. The base system 100 depicted in FIG. 1B additionally includes a physical user input device 120 (e.g., keyboard with trackpad), a video camera 122 distinct from the display such as a Logitech HD Webcam C615 available from Logitech of Newark, Calif., and a power supply 150. In the embodiment depicted in FIG. 1B, a single receptacle module 106 is configured to support multiple augmented instruments, e.g., otoscope 120 and ophthalmoscope 130.

Figure 2B:
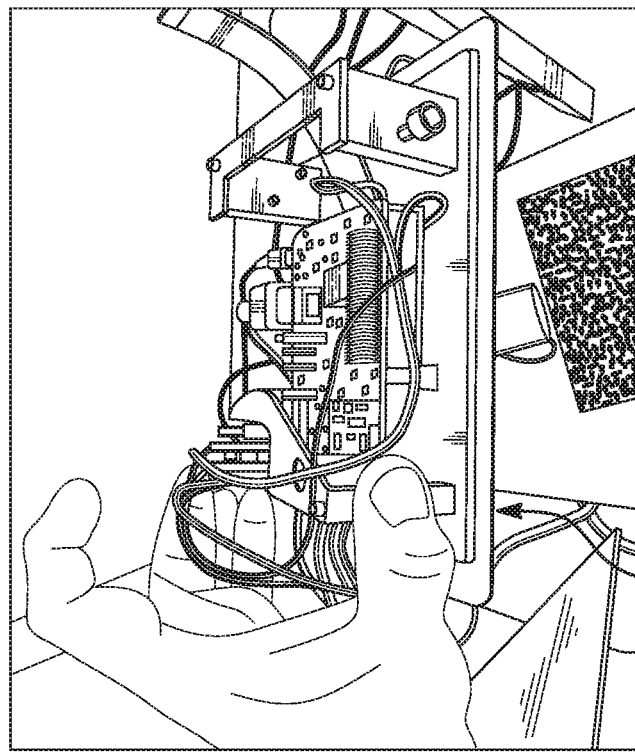
FIG. 2B is a back perspective view of the display of FIG. 2A with a controller within the control module attached to the display.
Figure 2A:
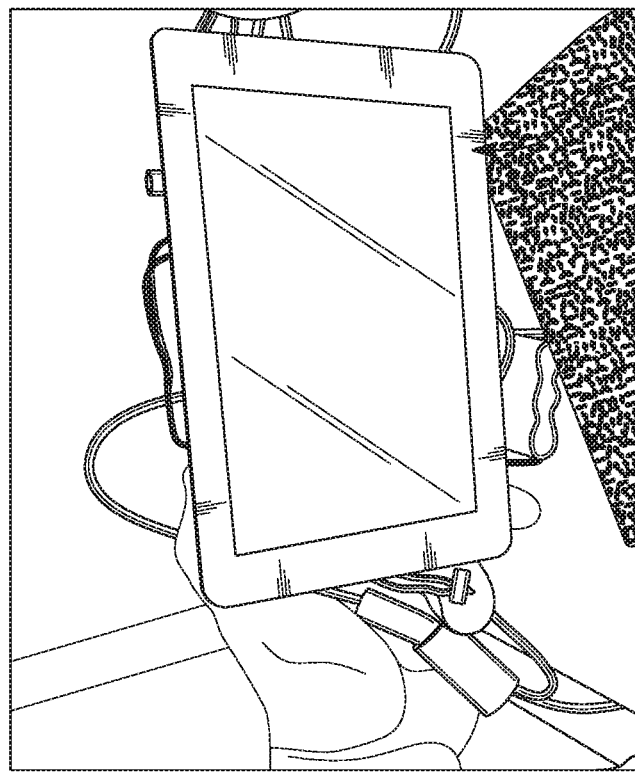
FIG. 2A is a front perspective view of a display within the control module of the base system of FIG. 1A.

FIG. 2A depicts a front view of the touchscreen 110 and FIG. 2B depicts a rear view of the touchscreen 110. The control module 104 (FIG. 1A) includes a controller, a power supply and a communication interface(s), which may be mounted to the back of the touchscreen 110 as visible in FIG. 2B. The communication interface may provide wired and/or wireless communication with one or more of the augmented instruments. The communication interface may include multiple communication mediums, e.g., Bluetooth, USB, NFC, Ethernet, etc. A suitable controller is the Raspberry Pi 3 Single board computer running an operating system such as Linux or Windows available from Adafruit Industries, LLC of New York, N.Y. and a suitable wireless communication interface is a Bluetooth com-Blue SmiRF wireless serial communications module available from SparkFun Electronics of Niwot, Colo. The power supply may be a conventional power supply (e.g., a 3.5 V or 5V DC power supply) that is coupled to the power supply of the base system 100 for powering the control module 104.

The control module 104 is configured for control by the user interface and to conduct training and/or performance assessment sessions, communicate with the augmented instruments, collect data (e.g., examination data) from the augmented instruments, process and store data and communicate data to a server, which may be remote from the base system 100. Data received from augmented instruments may be formatted in a text file format (e.g., comma separated values; CSV). Communication with augmented instruments may be conducted using specific addresses associated with each augmented instrument to distinguish between augmented instruments and to avoid communication errors.

Details regarding augmented instruments are now provided. As a general overview, each augmented instrument may have one or more sensors, a battery, a microcontroller and a communication module. Sensors may include optical sensors, audio sensors, position sensors, distance sensors, and/or orientation sensors for collecting examination data. The microcontroller is configured to drive sensor(s), collect data, and communicate the data to the control module 104 of the base system 100. Examination data collected from the sensors by the microcontroller is communicated to the base system 100 via a wired connection and/or via a wired connection, e.g., via Bluetooth. The data may be temporarily stored in a storage device within an augmented instrument by the microcontroller for subsequent transmission to the base system 100, e.g., after an examination. Other wireless technology such as near field communications (NFC) and/or wired technology such as universal serial bus (USB) or Ethernet may be used for data transfer and/or battery charging.

Distance sensors may be incorporated into one or more augmented instruments to determine position, e.g., to an accuracy within 1 mm over a range of 3 to 20 centimeters and orientation sensors may be incorporated into one or more augmented instruments to determine angular rotation, e.g., in 3 axes to better than 1 degree.

Figure 3B:
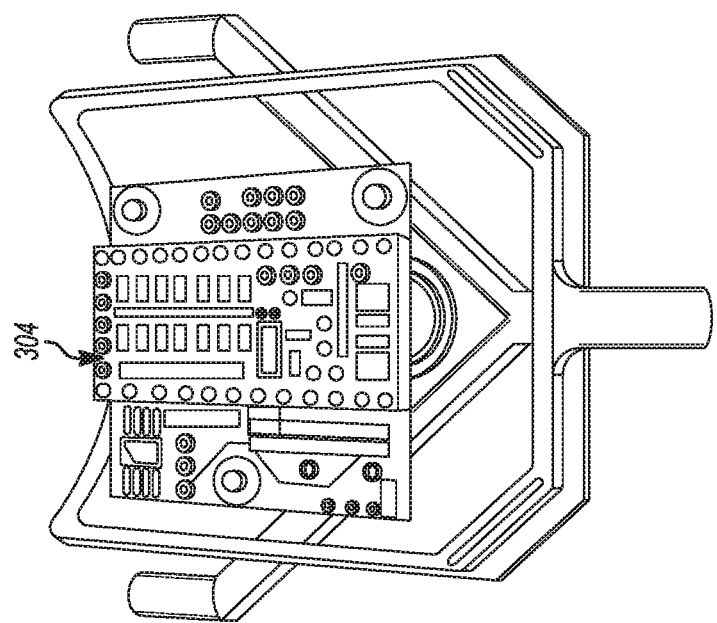
FIG. 3B is an enlarged view of the control module of the stethoscope of FIG. 3A.
Figure 3A:
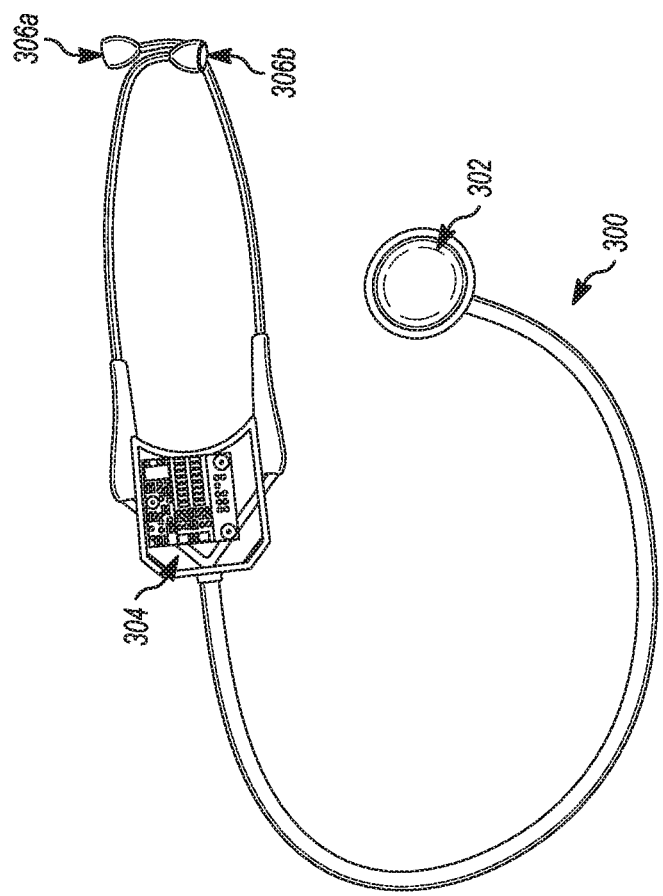
FIG. 3A is an illustration of a stethoscope in accordance with aspects of the invention.

FIG. 3A depicts an augmented stethoscope 300 in accordance with aspects of the invention. The stethoscope 300 includes a chest piece 302, a control module 304, and ear pieces 306a and 306b. FIG. 3B depicts an enlarged view of the control module 304. During use, a student places the chest piece 302 on the body of a subject and listens through the ear pieces. In an embodiment, the stethoscope operates as a conventional analogue stethoscope with pass-through sound with the addition of digital recording, digital playback of recordings, wireless connectivity (e.g., Bluetooth), and/or sound overlay, which is described in further detail below.

Figure 3C:
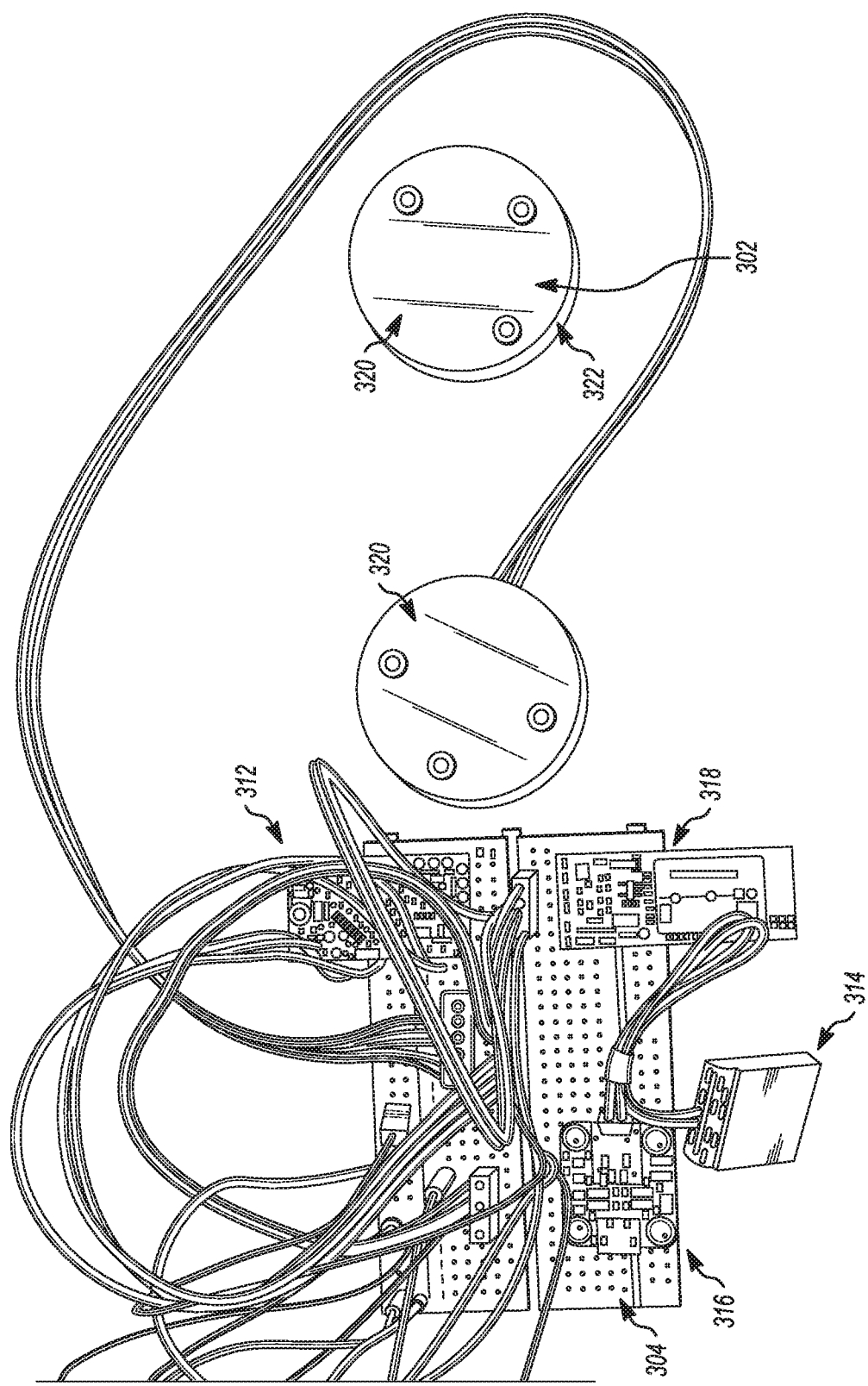
FIG. 3C is an image of components incorporated into the stethoscope of FIG. 3A.

As depicted in FIG. 3C, the augmented stethoscope 300 may include a controller 312, a battery 314, a battery charger 316, a Bluetooth communication module 318, an accelerometer 320, and a microphone 322. The microphone 322 is integrated into the chest piece 302 to pick up sounds during an examination. The Bluetooth communication module 306 is configured for communication with the control module 104 of the base system 100 via Bluetooth. Additionally, the Bluetooth communication module may be used to provide sound to a student/examinee via headphones (not shown) or speakers located in ear pieces 306a and/or 306b. The battery may be a Lithium Ion rechargeable battery that is capable of operating device for 2 or more hours.

The controller 312 is configured to record, analyze, and playback sound waves over Bluetooth antennas. The chest piece 302 includes voids and compartments to house electronic sensors such the accelerometers 320 and microphone 322 to provide functionality.

Suitable microcontrollers include the Arduino Pro Mini available from SparkFun Electronics of Niwot, Colo. and the Teensy 3.2 available from Adafruit Industries, LLC of New York, N.Y., which can sample audio at 44 kHz, making them capable of even performing voice recognition. Suitable microphones include the Electret microphone available from Adafrult, which comes with an embedded amplifier "Voice Changer" and a "Fast Fourier Transform" analyzer using the Teensy 3.2 microcontroller.

A storage device within the Bluetooth module 306 is configured to store data collected during each training session. The stored data may then be transferred to the controller 104.

A suitable accelerometer 320 is an xyz accelerometers which provides 3 axis of rotation with 2 degrees of freedom such as a SparkFun Triple Axis Accelerometer Breakout—ADXL335 available from SparkFun Electronics of Niwot, Colo.

Figure 3F:
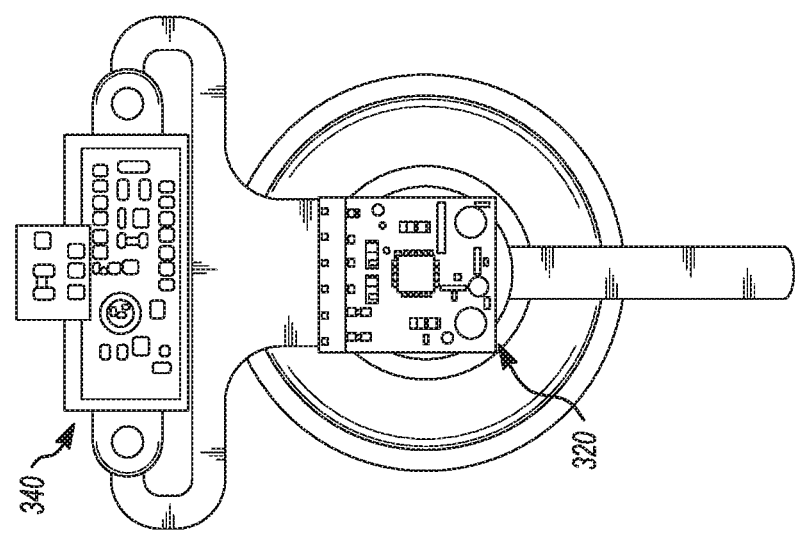
FIGS. 3D, 3E, and 3F are bottom, side, and top views, respectively, of a chest piece of a stethoscope in accordance with aspects of the invention.
Figure 3E:
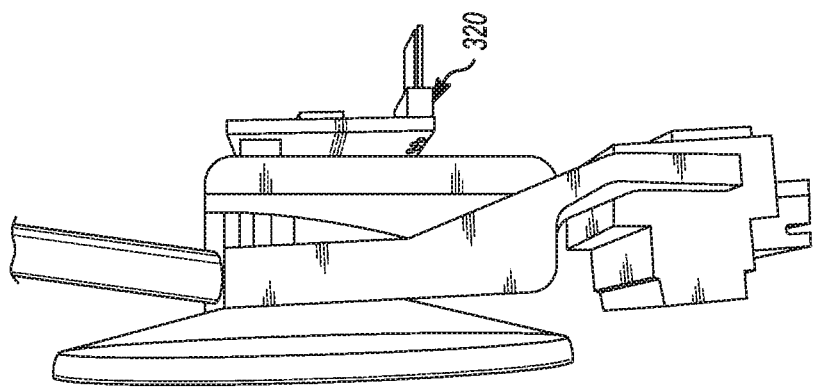
Figure 3D:
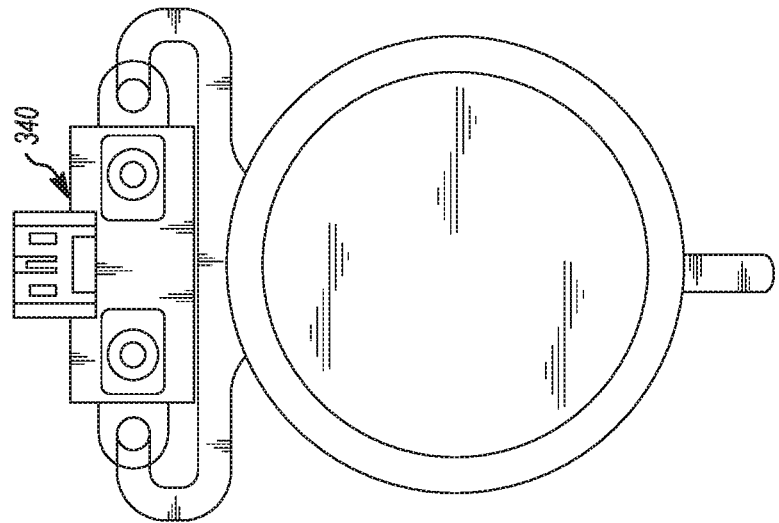

FIGS. 3D, 3E, and 3F depict another chest piece 302 for use with an augmented stethoscope in accordance with aspects of the invention. The chest piece 302 includes a distance sensor 340 (e.g., an IR Proximity sensor) in addition to the accelerometers 320. A suitable distance sensor 340 is an IR distance sensor such as a GP2Y0E02A IR Range Sensor—4 cm to 50 cm (Analogue Output) available from SparkFun Electronics of Niwot, Colo. The SHARP Proximity sensor uses infra-red technology to determine the relative position of the diaphragm, which can be used to evaluate correct placement of the instrument. A suitable accelerometer is an Analog Devices ADXL335 3-axis accelerometer available from SparkFun Electronics of Niwot, Colo. The accelerometer can be used to determine the instrument orientation.

Examination data gathered from the sensors may be used to assess performance of a student during an examination. For example, a conventional scenario for using a stethoscope involves auscultation. Auscultation is the action of listening to internal sounds of the body (e.g., heart, lung, and other organ sounds. Each organ has a unique signature that may be heard at different locations on the body. Different sounds may need to be observed for different periods of time to properly identify different organs and/or to diagnose the quality and/or possible problems associated the identified organ. Heart sounds are primarily observed in five discrete location on the chest. Lungs sounds are primarily observed at seven locations on the chest and seven locations on the back. For example, during a training/assessment session, the student may be instructed to examiner the heart and lungs of a patient. In accordance with this scenario, the examination data available from the distance sensor would indicate how long the chest piece was positioned against the body of the patient (e.g., the time that the distance equals approximately zero) and the accelerometer would indicate how long the chest piece was stationary during this period of time. This examination data could then be compared to stored data for the scenario to indicate whether the chest piece was positioned correctly for the required period of time (e.g., at least two seconds at each position.

Additionally, live heart and/or lung sound (and/or electrical impulse) detection can be used to ensure correct placement of the stethoscope. Audio (and/or electrical) waveforms produced by the heart and lungs produce a signature that is indicative of position. Signatures obtained by an augmented stethoscope can be compared to stored signatures. If there is a match, it can be concluded that the chest piece was correctly positioned.

Also, waveforms produced by the heart and/or lungs can be indicative of pathologies. Pathology waveforms (such as a waveform associated with a heart murmur) may be stored in a database. During particular scenarios, one or more of these pathology waveforms may be presented to the examinee by replacing an actual heart signal with the stored waveform or overlaying the actual heart signal with the stored waveform. The examinee may be asked to identify the pathology based on the waveform presented to the examinee.

Figure 3G:
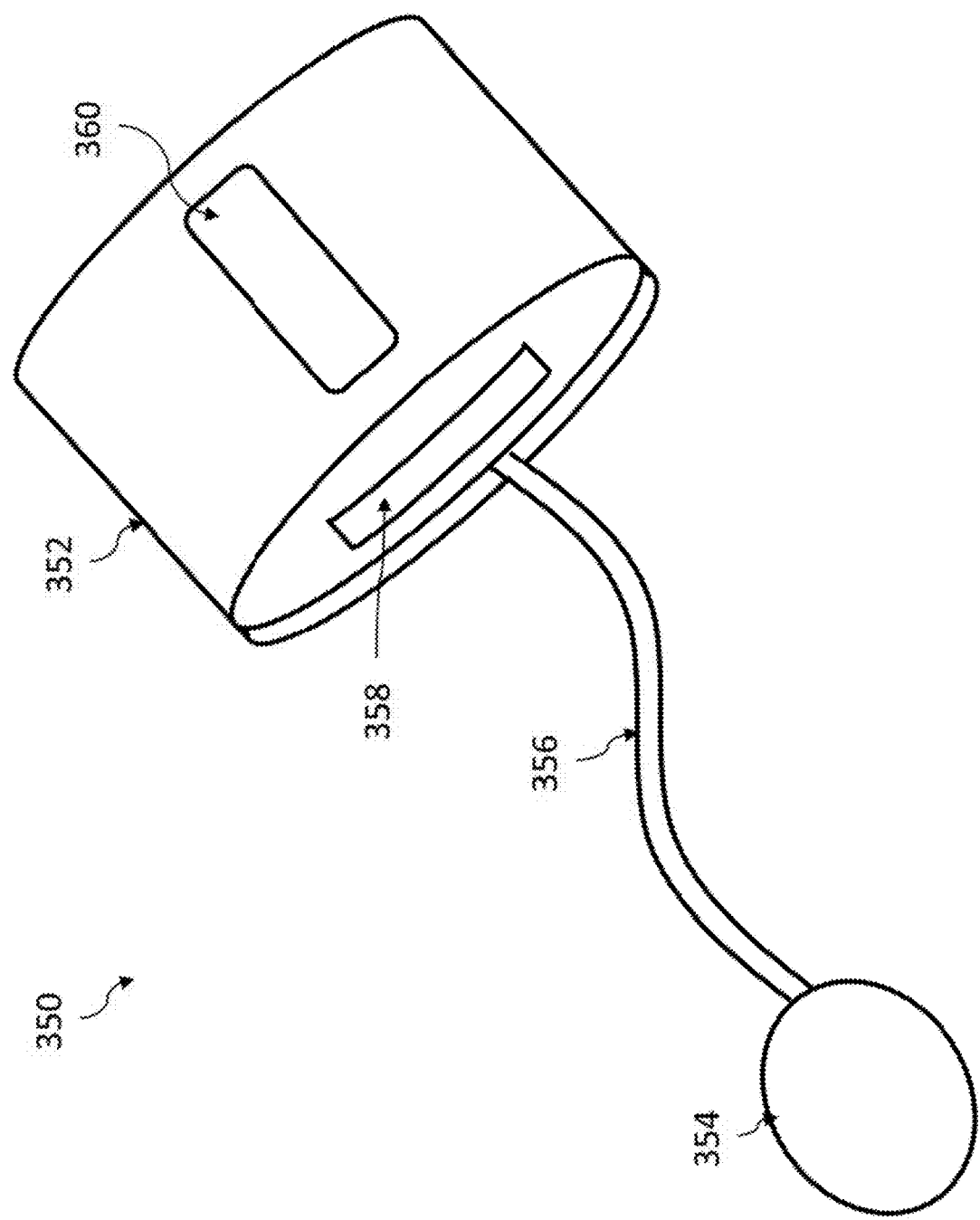
FIG. 3G depicts an augmented blood pressure module according to aspects of the invention.

FIG. 3G illustrates an augmented blood pressure module 350 in accordance with aspects of the invention. Augmented blood pressure module 350 includes a pressure cuff 352, a pump 354, a hose 356 connecting pump 354 to pressure cuff 352, and a display 360. Augmented blood pressure module 350 includes at least one sensor 358 configured to measure the pressure applied to a patient's arm and/or sense the patient's heartbeats and/or heartrate. For example, sensor 358 of augmented blood pressure module 350 may include a pressure transducer configured to sense a pressure and produce a corresponding analog signal. The augmented blood pressure module 350 may store the sensed examination data relating to the applied pressure and/or the patient's heartbeats using, e.g., an on-board volatile or non-volatile memory for short and/or long-term data storage. Display 360 may be an analog or digital screen configured for displaying, in real-time or at predetermined time intervals, the applied pressure and/or the patient's heartbeats/heartrate to the student.

Augmented blood pressure module 350 may be used in conjunction with augmented stethoscope module 300. For example, a student may operate the augmented blood pressure module 350 and use augmented stethoscope module 300 to hear the Korotkoff sounds from the artery of the patient or the augmented Korotkoff sounds produced by the augmented device (e.g., augmented blood pressure module 350 and/or augmented stethoscope module 300). In one embodiment, augmented blood pressure module 350 and augmented stethoscope module 300 are configured to communicate with control module 104 for augmented functionalities, such as for simulating a predetermined blood pressure that is to be perceived by the student. The simulated physical parameters corresponding to audio content (e.g., sounds) may correlate to the blood pressure of the patient so that the student hears the appropriate sounds at the appropriate pressures. In one embodiment, the simulated physical parameters (e.g. corresponding to or based on augmented data, which is further discussed herein) are synchronized to the patient's actual heartbeat such that the augmented simulation appears realistic even if the pulse is being palpitated/monitored by the student.

Figure 4:
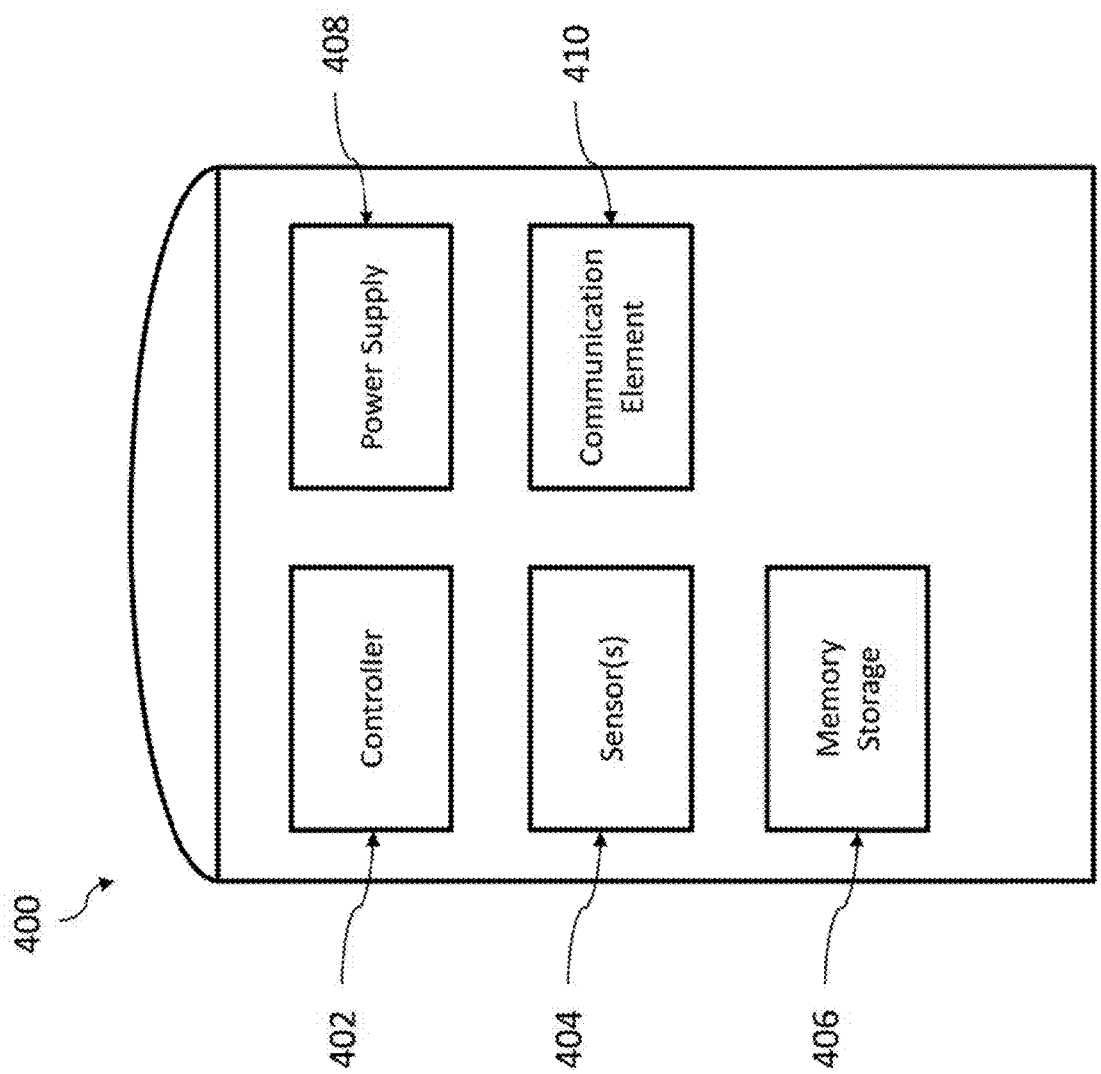
FIG. 4 depicts an augmented handle module in accordance with aspects of the invention.

FIG. 4 depicts an augmented handle module 400 in accordance with an example of the invention. Augmented handle module 400 includes a controller 402, at least one sensor 404, a memory storage 406, a power supply 408, and communication element 410. Augmented handle module 400 may have the shape and functionality of a standard ophthalmoscope or otoscope handle, including a power supply 408 to provide electricity to one or more components of an ophthalmoscope headpiece (e.g. augmented ophthalmoscope module 500) or otoscope headpiece (e.g., augmented otoscope module 450). In one embodiment, power supply 408 includes batteries and a charging module for recharging such batteries. Augmented handle module 400 includes embedded electronics configured for enabling augmented functionalities, such as a controller 402 and sensor(s) 404.

Controller 402 of augmented handle module 400 is configured to trigger and/or interact with one or more components of augmented handle module 400. For example, controller 402 may trigger and/or interact with power supply 408, sensor(s) 404 of augmented handle 400, and/or memory storage 406. Additionally or alternatively, controller 402 may trigger and/or interact with the one or more sensors, including but not limited to the sensor(s) of an ophthalmoscope headpiece or otoscope headpiece, by obtaining examination data from such sensor(s) and/or by initializing such sensor(s).

Augmented handle module 400 includes at least one sensor 404. Sensor 404 of augmented handle 400 may be configured to measure the distance between augmented handle 400 and a nearby object (e.g., an object for a student to employ the device on, such as a patient), measure acceleration, measure angular velocity, and/or determine an orientation of the augmented handle. For example, augmented handle module 400 may include a Time of Flight ("TOF") sensor, a proximity/distance sensor, and/or an Inertial Motion Unit ("IMU") sensor.

Augmented handle module 400 includes a memory storage 406, which may be utilized for storing data received from controller 402, sensor(s) 404, and/or communication element 410. Memory storage 406 may include a temporary storage element and/or a permanent storage element. Additionally or alternatively, memory storage 406 may transmit data to another device for storage, e.g., by way of communication element 410. Although communication element 410 is illustrates as a wireless element in FIG. 4, the communication element may include and/or connect via a wired connections in another embodiment of the invention.

Augmented data is prerecorded or predetermined data (e.g., data corresponding to a cataract, heart mummer, etc.) that is used to produce at least one simulated physical parameter. A simulated physical parameter is a modification of examination data corresponding to a sensed physical parameter and/or the combination of examination data and augmented data by modifying, overlying, modulating, blending, and/or replacing examination data with augmented data (e.g., such as overlying the examination data corresponding to the real-time imaging of a patient's eye with a prerecorded image of a cataract). Augmented handle module 400 is configured to provide augmented functionalities. The augmented functionalities include generating simulated physical parameters to be perceived (e.g., visually, audibly, etc.) by the student regarding the operation of the augmented device (e.g., ophthalmoscope module 500 or the augmented otoscope module 400). The augmented functionalities may include modifying, modulating, replacing, blending, or overlaying examination data with augmented data (e.g., prerecorded and/or predetermined data/information) to generate the simulated physical parameters that are presented to the student as visual content and/or audio content. In one embodiment, simulated physical parameters may be generated by modifying the examination data without employing augmented.

Controller 402 may trigger augmented functionalities based on an external trigger/signal received from control module 104. Alternatively or additionally, controller 402 may trigger augmented functionalities based on the examination data received from the at least one sensor. For example, controller 402 may trigger augmented functionalities based on examination data received from sensor 404 indicating that the augmented handle module 400 satisfies a threshold of distance from an object. By way of another example, controller 402 may trigger augmented functionalities, such as modifying the visual content displayed to the student (e.g., directly or indirectly through modifying the examination data), based on inertial motion data received from sensor 404 indicating that augmented handle module 400 is moving and/or rotating in space.

Figure 5A:
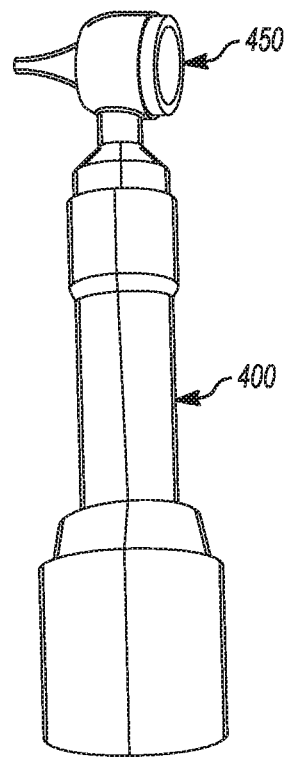
FIG. 5A is an illustration of an otoscope in accordance with aspects of the invention.

FIG. 5A depicts an augmented otoscope 400 in accordance with aspects of the invention. The augmented otoscope is configured to operate as a conventional otoscope with the addition of orientation and distance sensing. The illustrated otoscope 400 includes an otoscope head unit 450 and an augmented handle module 400. The otoscope head unit 450 includes optics (such as Reister CE optics available from Riester Direct of Ventura, Calif.). The augmented handle module 400 is configured for attachment to the otoscope head unit 450 to obtain and provide orientation and distance sensing.

Figure 5C:
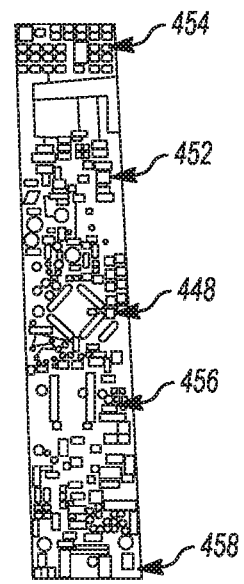
FIG. 5C is an enlarged view of the sensor module in the base of the otoscope of FIG. 5B.
Figure 5B:
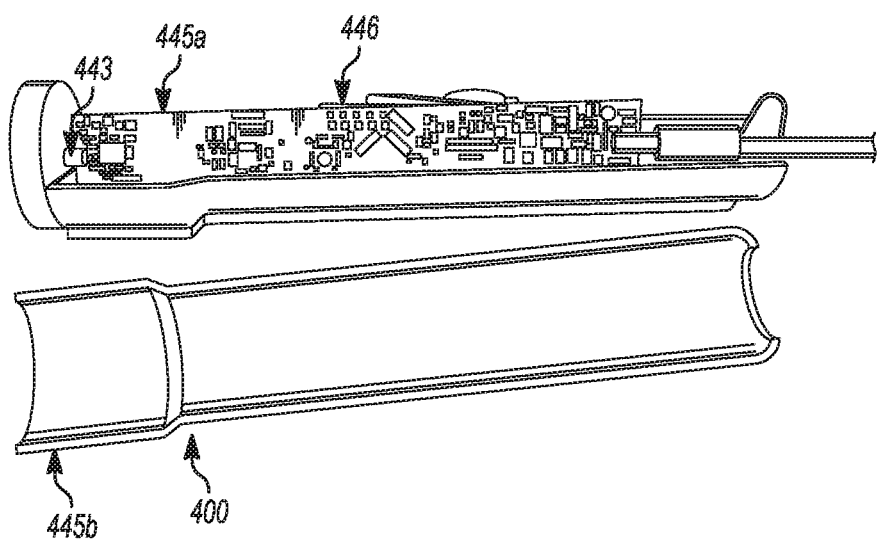
FIG. 5B is a partially disassembled view of a base of an otoscope in accordance with aspects of the invention.

FIG. 5B depicts a disassembled view of the augmented handle module 400. The illustrated smart handle 400 includes a two-part housing having a support portion 445a and a cover portion 445b. The support portion 445a supports a sensor module 446. The augmented handle module may additionally include a light 443 (e.g., and LED), a battery, a battery charger, and a memory. The memory may be used to store data for one or more training/assessment sessions and then ported to the controller of the base unit, e.g., via a wired or wireless connection. Data capacity should be 30 minutes or greater to capture data during a typical examination. The augmented handle module 400 may be configured for connection to different head units, e.g., to otoscope head unit 450 and to ophthalmoscope head units, which are described below.

The battery may be a Lithium Ion rechargeable battery that is capable of operating device for at least 2 hours available from SparkFun Electronics of Niwot, Colo. This is a very small, extremely light weight battery based on Polymer Lithium Ion chemistry. This is the highest energy density currently in production. Each cells outputs a nominal 3.7V at 400 mAh. The dimensions of the battery are 5×25×35 mm.

FIG. 5C provides an enlarged view of the sensor module 446. The sensor module 446 includes a microprocessor 448, a USB connection 458, an inertial measurement unit (IMU) 452, a distance sensor 454, and an FTDI interface 456 available from Future Technology Devices International of Glasgo, Scotland.

The microprocessor 448 may be an Arduino pro mini Controller-Arduino mini available from Adafruit Industries, LLC of New York, N.Y. The Arduino Pro Mini is a microcontroller board based on the ATmega328 (datasheet). It has 14 digital input/output pins (of which 6 can be used as PWM outputs), 6 analog inputs, an on-board resonator, a reset button, and holes for mounting pin headers. A six pin header can be connected to an FTDI cable or Sparkfun breakout board to provide USB power and communication to the board.

The distance sensor 454 may be an IR proximity sensor capable of measuring 4-30 cm with 2 mm resolution available from Adafruit Industries, LLC of New York City, N.Y. An angular sensor (not shown) may also be incorporated into the augmented handle module. The angular sensor may have 3 axis of rotation with 2 degree resolution available from SparkFun Electronics of Niwot, Colo.

The distance sensor 454 may provide measurement of how close the student brings the scope to the ear of the subject. These sensors have a range of about 3 to 30 centimeters with a resolution of 0.2 mm. These can be used to measure actual distance or set up to indicate when the scope is within a distance threshold. The sensors may be pulsed at 20 milliseconds for 10 measurements. Time may also be recorded to document when and how long the student held the scope within range to the subject.

The otoscope is configured to provide data (e.g., examination data) for when the student is using it, orientation to indicate looking up or down and distance sensing to determine how far the scope is from the face of the subject. Data acquisition may be activated when the otoscope is removed from the wall mount instrument panel and continues until replaced or timed out. Data may be acquired at 50 millisecond intervals and written to a csv file format.

Figure 6A:
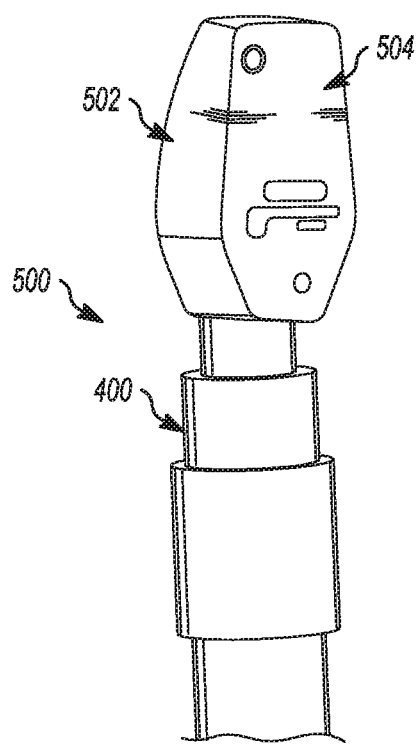
FIG. 6A is an image of a ophthalmoscope in accordance with aspects of the invention
Figure 6B:
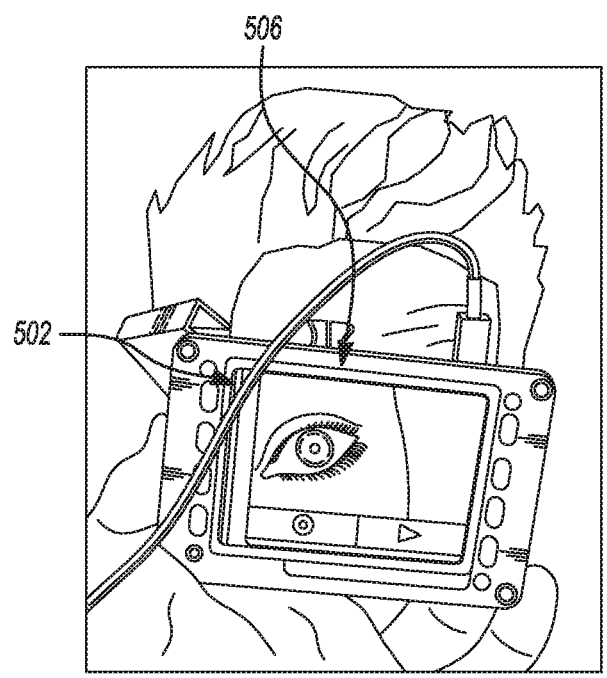
FIG. 6B is a view of a display for use with the ophthalmoscope of FIG. 6A.

FIG. 6A depicts an augmented ophthalmoscope 500 in accordance with aspects of the invention. The augmented ophthalmoscope is configured to operate as a conventional digital ophthalmoscope with the addition of orientation and distance sensing. The illustrated ophthalmoscope 500 includes an ophthalmoscope head unit 500 and the augmented handle module 400. The ophthalmoscope head unit 500 includes an optics receiving port 504 and an image display 506 (FIG. 6B). The augmented handle module 400 is configured for attachment to the ophthalmoscope head unit 502 to obtain and provide orientation and distance sensing.

Figure 6C:
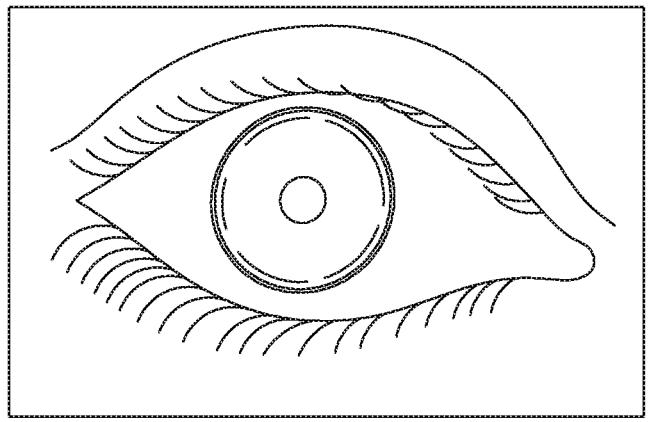
FIG. 6C is an image of a normal eye being viewed with the ophthalmoscope of FIG. 6A.
Figure 6D:
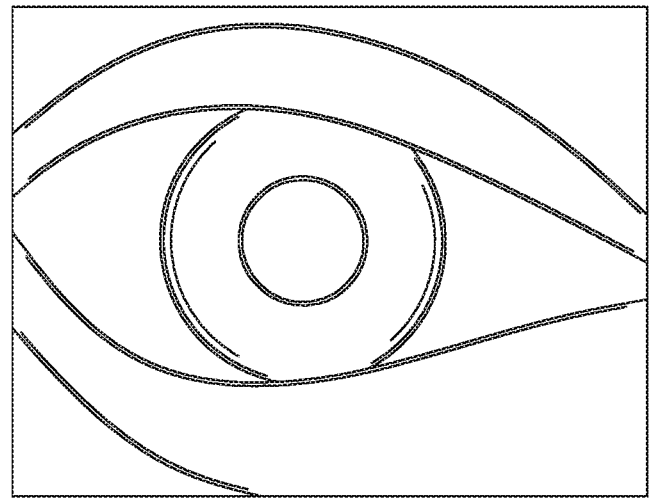
FIG. 6D is an image of a pathologic eye being viewed with the ophthalmoscope of FIG. 6A.

In an embodiment, the augmented ophthalmoscope 500 includes optics to operate as a conventional ophthalmoscope with the addition of orientation and distance sensing, which may be provided through the smart handle 400. The ophthalmoscope may depict real-time and/or recorded video images, e.g., to overly a normal eye (FIG. 6C) sensed live/in real-time via the optics receiving port 504 with a pathologic image (FIG. 6D). Sensors may be used to switch from a real-time to overlay image. For example, sensed ambient light level indications and object recognition algorithms may be used to change an overlay image to match pupil size, color, and position.

Figure 7:
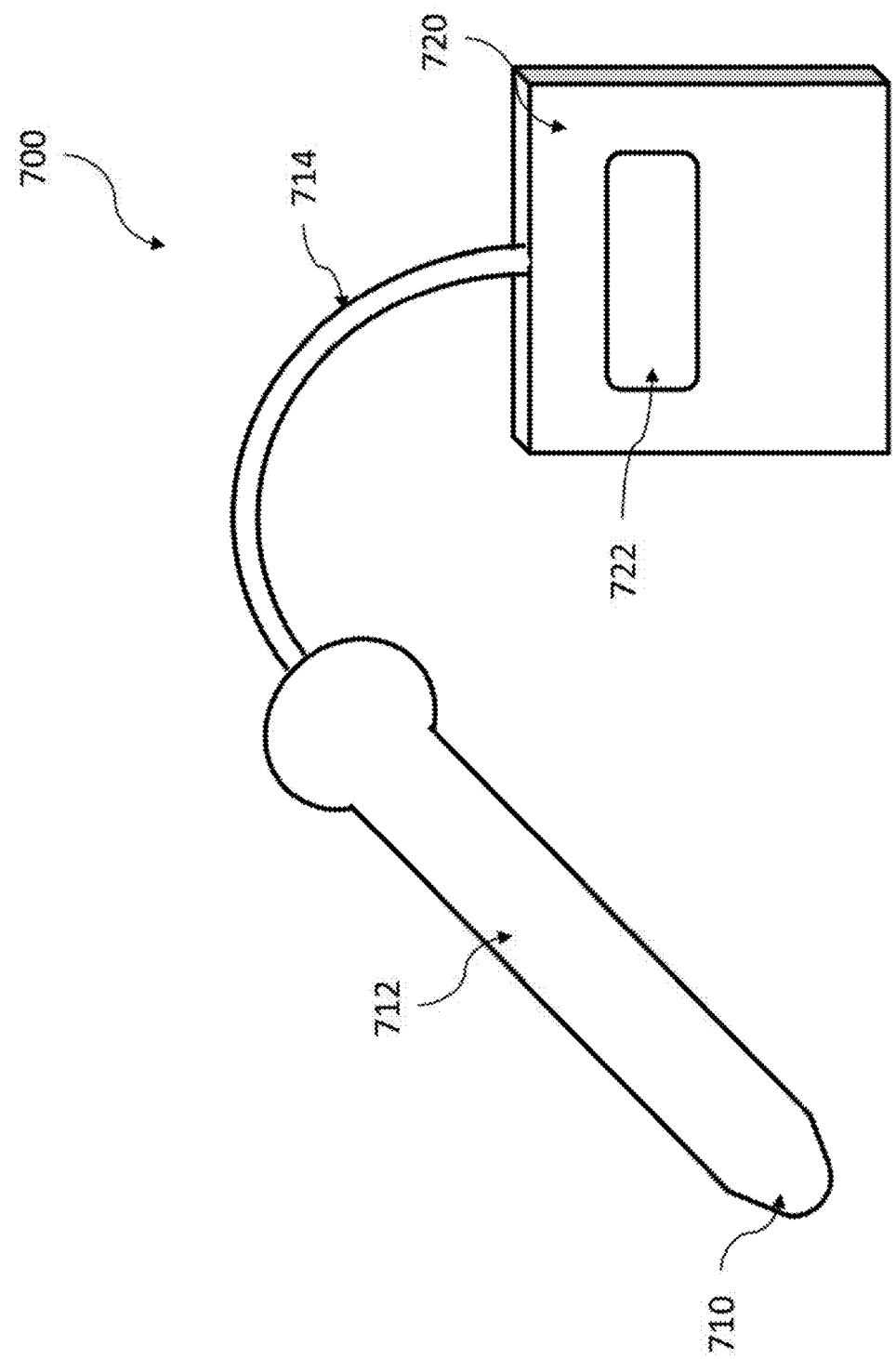
FIG. 7 depicts an augmented thermometer in accordance with aspects of the invention.

FIG. 7 depicts an augmented thermometer 700 according to aspects of the invention. Augmented thermometer 700 includes at least one sensor 710 and a base 720 connected to the at least one sensor 710. Augmented thermometer 700 may have the shape and functionality of a standard thermometer. For example, sensor 710 may be incorporated into a sensor rod 712 configured to resemble a standard thermometer shape and to facilitate the insertion of augmented thermometer 700 into a patient's orifice, e.g., under a patient's tongue. Although sensor 710 and sensor rod 712 are connected to base 720 by wire 714 in the embodiment illustrated in FIG. 7, sensor 710 may be connected wirelessly to base 720 in another embodiment of the invention. Additionally or alternatively, sensor 710 may include a thermocouple and/or include any other component(s) suitable for sensing the temperature of a patient.

Base 720 of an augmented thermometer 700 may include memory storage and a display 722. Base 720 may store sensed data (e.g., examination) relating to the temperature of the patient using, e.g., an on-board volatile or non-volatile memory for short and/or long-term data storage. Display 722 may be an analogous or a digital screen configured for displaying the patient's temperature in real-time or at predetermined time intervals.

Figure 8:
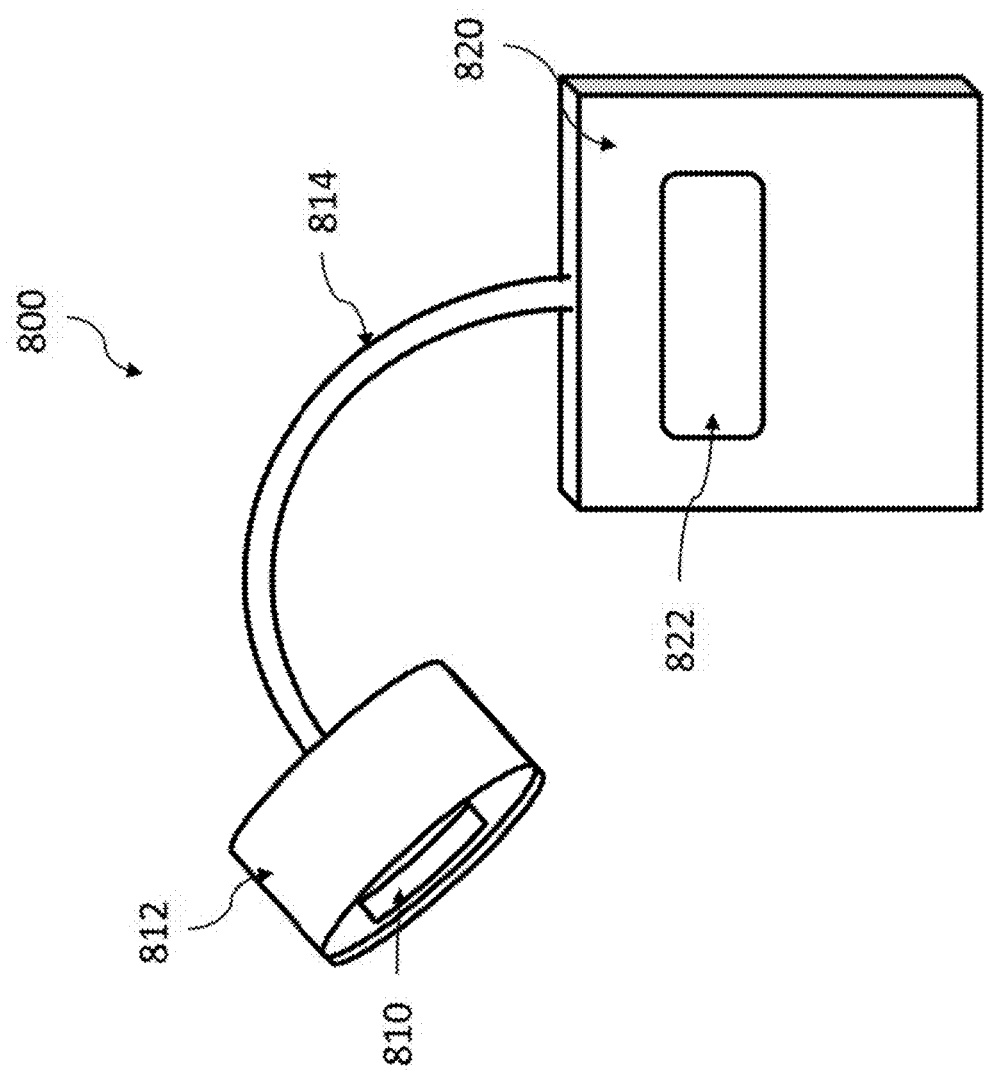
FIG. 8 depicts an augmented pulse oximeter according to aspects of the invention.
Figure 9:
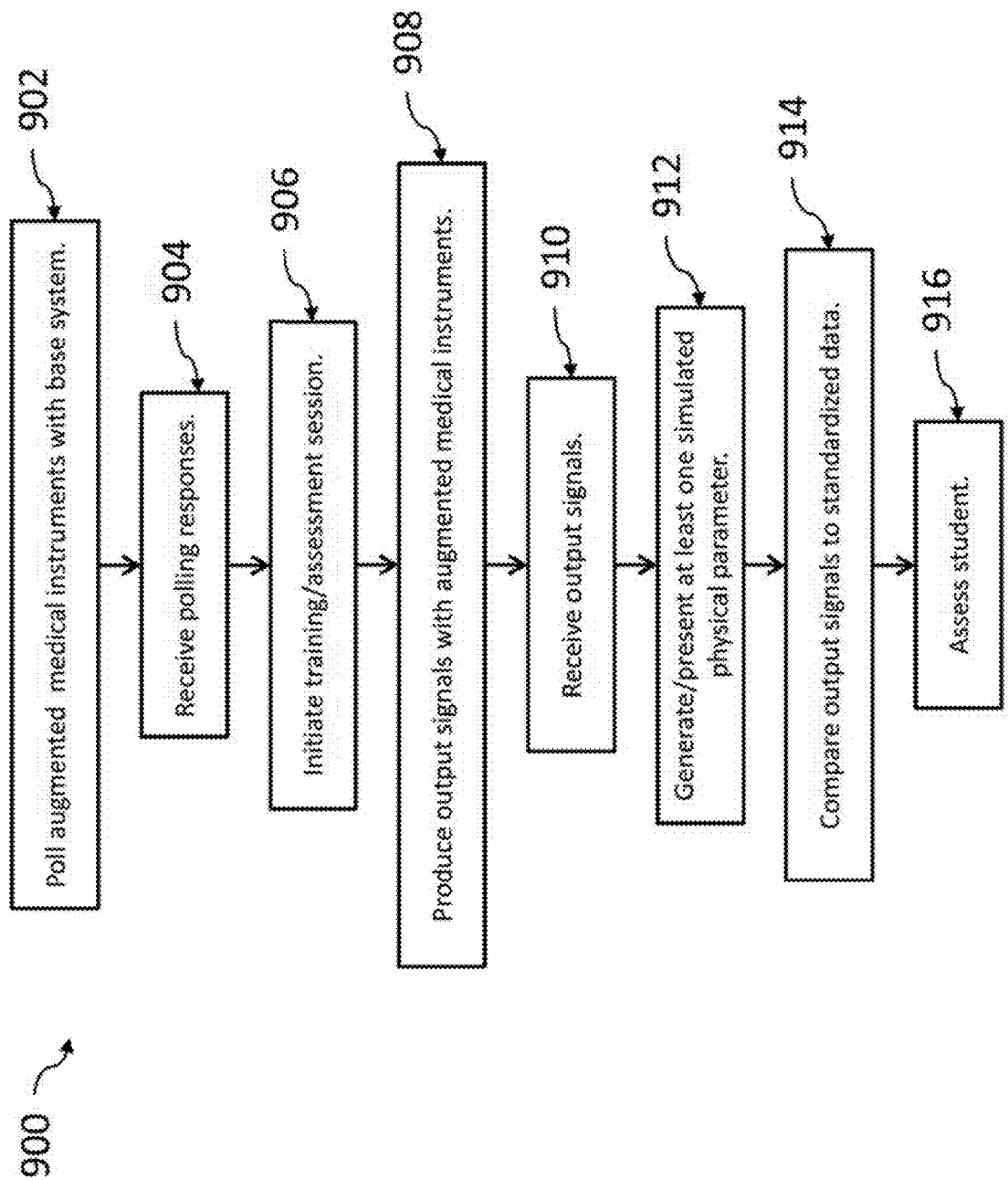
FIG. 9 is a flowchart of a medical method for training and/or assessing students using augmented devices in accordance with aspects of the invention.

FIG. 8 depicts an augmented pulse oximeter 800 according to aspects of the invention. Augmented pulse oximeter 800 includes at least one sensor 810 and a base 820 connected to the at least one sensor 810. Augmented pulse oximeter 800 may have the shape and functionality of a standard pulse oximeter. For example, sensor 810 may be incorporated into a finger clasp 812 configured to resemble a standard pulse oximeter and to facilitate placement of the augmented pulse oximeter 800 at least partially around the patient's finger. Although sensor 810 and finger clasp 812 are connected to base 820 by wire 814 in the embodiment illustrated in FIG. 8, sensor 810 is connected wirelessly to base 820 in another embodiment of the invention.

Base 820 of an augmented pulse oximeter 800 may include memory storage and a display 822. Base 820 may store sensed data (e.g., examination data) relating to the heartrate, heartbeats, temperature, and/or oxygen saturation of a patient, e.g., an on-board volatile or non-volatile memory for short and/or long-term data storage. Display 822 may be an analogous or a digital screen configured for displaying the patient's temperature in real-time or at predetermined time intervals.

FIGS. 9-15 depicts flowcharts 900, 1000, 1100, 1200, 1300, 1400, and 1500 of steps for training and/or assessing the performance of a student. Although the steps of flowcharts 900, 1000, 1100, 1200, 1300, 1400, and 1500 are described with reference to the systems and instruments illustrated in FIGS. 1-8, it will be understood from the description herein that the steps may be practiced using other systems/instruments. Furthermore, one or more of the steps may be omitted and/or performed in an order other than depicted in FIGS. 9-15 without departing from the scope of the invention.

At step 902, the augmented medical instruments are polled. Control module 104 of base system 100 may poll augmented instruments such as an augmented ophthalmoscope 130, an augmented otoscope 120, and an augmented stethoscope 140. Control module 104 may transmit a polling signal (e.g., via Bluetooth) for receipt by the augmented instruments. Control module 104 may be configured to poll the augmented instruments when the control module is activated and/or between each training/assessment session.

As step 904, polling results are received. Control module 104 may receive the polling results in the form of responses from the augmented instrument. Each augmented instrument may be configured to respond to polling signals with a unique response indicative of that augmented instrument. For example, may send a communication that includes a module ID number or a type of module ID number from which the control module can determine the type of augmented instruments available. Control module 104 may maintain a table in memory of available augmented instruments. At step 906, a training and/or performance assessment session is initiated. A session may be initiated by a student or by an instructor via a touchscreen of control module 104 or via another user input, e.g., a keypad. A session may be initiated by selecting the session from a list of sessions displayed by control module 104. In response to selection of a session, control module 104 may determine the types of augmented instruments required to complete the session (e.g., by reviewing a list of requirement associated with the session that are stored in memory) and compare the required augmented instruments to the available augmented instruments. If all required augmented instruments are available, control module 104 will proceed with the session. If any required augmented instruments are not available, control module 104 will issue an alert (e.g., audio or video) so that corrective actions can be performed.

For a training session, the student may be presented with step-by-step instructions for performing a particular procedure (e.g., a basic male physical). For an assessment session, the student may be instructed to perform a particular procedure without be provided the step-by-step instructions.

At step 908, output signals including examination data are produced by the augmented medical instruments. The examination data corresponds to sensed physical parameters including, e.g., physiological parameters, distance, orientation, temperature, pressure, size of one or more of the patient's features, and environmental conditions. Environmental conditions may include background information (e.g., audible background noise, the temperature of room, etc.). Each augmented medical instrument produces information associated with use of the augmented medical instrument. In an embodiment, an augmented instrument may begin generating examination data when it is removed from an augmented instrument receptacle module 106 and continue to generate examination data until it is replaced in the augmented instrument receptacle module 106. In an alternative embodiment, the augmented instruments generate examination data responsive to control signals received from control module 104. For example, control module may instruct the augmented otoscope 120 to generate examination data during the session when the augmented otoscope 120 should be used by the student and instruct the augmented ophthalmoscope 130 to generate examination data during the session when the augmented ophthalmoscope 130 should be used by the student.

The augmented medical instruments may continuously transmit their generated examination data by producing output signals including the examination data and transmitting the output signals (e.g., via Bluetooth or a wired connection). Alternatively, or additionally, the augmented instruments may store the generated examination data in a memory within the augmented instruments for subsequent production of output signals for transmission to control module 104. The augmented instruments may produce and transmit output signals periodically (e.g., every 10 minutes), at the end of each session, or when the augmented instrument in returned to an augmented instrument receptacle module 106.

At step 910, output signals including examination data are received at the base system. The control module 104 of base system 100 may receive the output signals produced by the augmented medical instruments via wireless and/or wired connections.

At step 912, at least one simulated physical parameter is generated and presented. An augmented instrument may generate simulated physical parameters on information from the subject being examined. The augmented instrument may generate the simulated physical parameters based on image and/or audio information received from control module 104. The augmented instrument may modify the received image and/or audio information based on information gathered from the subject and present the subject information with the simulated physical parameters to the student via the augmented instruments.

For example, an augmented ophthalmoscope may obtain an image of a cataract to be used as simulated physical parameters (e.g., from memory in the ophthalmoscope or from control module 104). During examination of a subject with normal eyes, the normal eye image obtained by the augmented ophthalmoscope may be overlaid (e.g., directly or indirectly by overlaying the examination data with prerecorded data) with simulated physical parameters generated by the augmented ophthalmoscope. The augmented ophthalmoscope may generate the simulated physical parameters by modifying the cataract image based on the normal eye image (e.g., to match tint and size of features of the eye).

In another example, an augmented stethoscope may obtain a recording of a heart murmur to be used as simulated physical parameters (e.g., from memory in the stethoscope or from control module 104). During examination of a subject with a normal heart, the normal sounds obtained by the augmented stethoscope may be overlaid (e.g., directly or indirectly by overlaying the examination data with prerecorded data) with simulated physical parameters generated by the augmented stethoscope. The augmented stethoscope may generate the simulated physical parameters by modifying the heart murmur based on the normal heart sounds (e.g., to match rhythm and strength.)

At step 914, output signals containing examination data are compared to standardized data. Control module 104 may compare the examination data within the output signals received from the augmented instruments for a session to standardized data associated with each step for that session. Each session may include standardized data including time ranges and positioning information ranges associated with optimal performance of each step of a particular procedure. The examination data may be compared to this standardized data to determine whether the student is optimally positioning the instrument for the optimal period of time.

At step 916, the student is assessed. Control module 104 may assess the student based on the comparison of the received examination data to the standardized data. The assessment may be generated by determining whether the examination data is within the ranges specified in the standardized data for each step of the procedure and, if they are outside a range for a particular step, the percentage of deviation from the range for that particular step. Control module 104 may generate a report including information summarizing compliance with the ranges associated with each step. The report may be communicated to the student and/or to a teacher/instructor.

Figure 10:
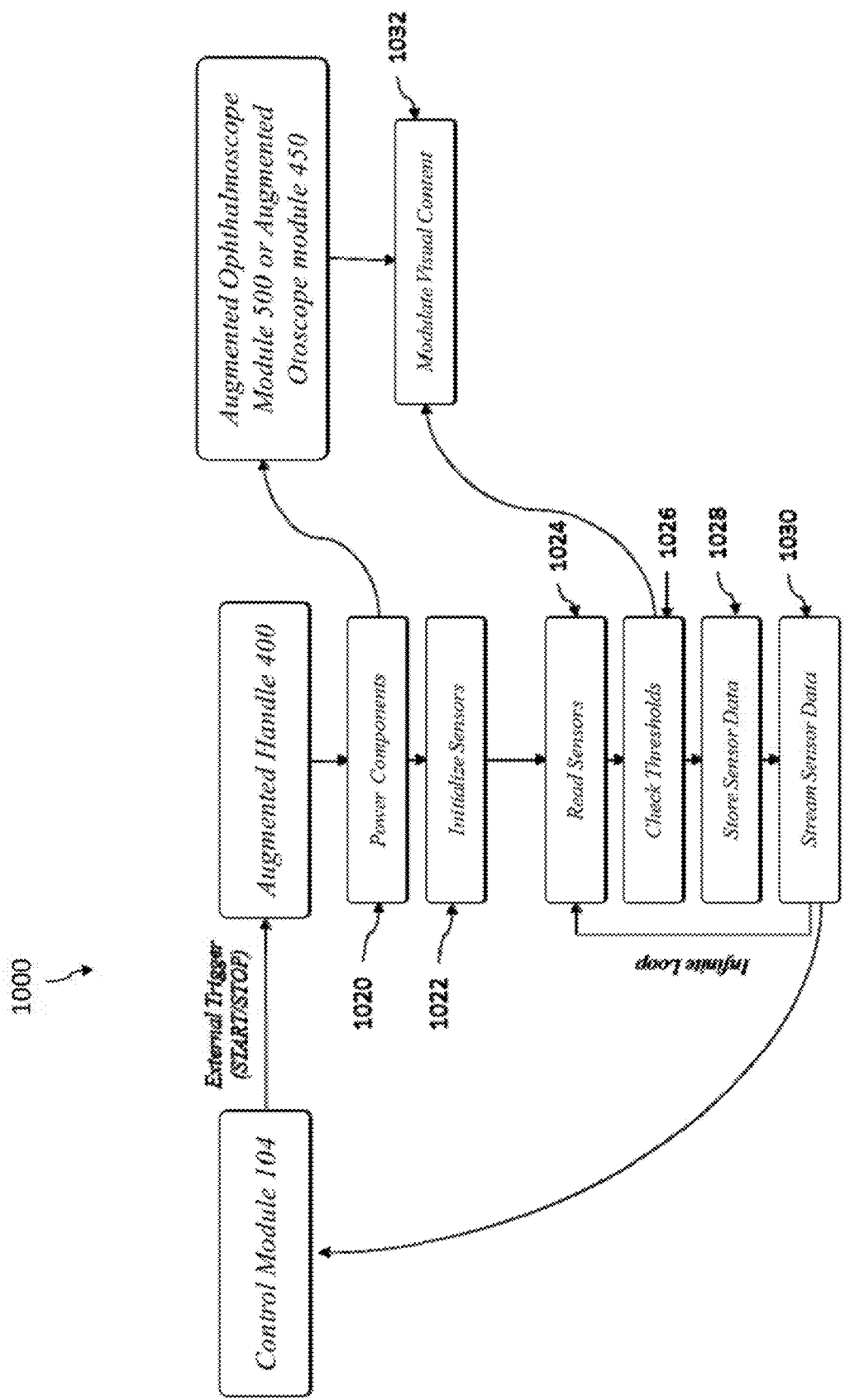
FIG. 10 is a schematic depicting a flowchart for utilizing an augmented handle module for assessing a student according to aspects of the invention.

FIG. 10 is a schematic depicting a flowchart 1000 for utilizing an augmented handle module 400 for assessing a student in accordance with aspects of the invention. Flowchart 1000 includes the steps of powering the components 1020, initializing the sensors 1022, reading the sensors 1024, checking the threshold(s) 1026, storing sensor data 1028, and streaming sensor data 430.

In step 1020, power is supplied to at least one component of the augmented handle module 400. A trigger for powering augmented handle module 400 may be provided such as an external trigger, e.g., a trigger initiated by control module 104, or an internal trigger initiated by controller 402. Additionally, augmented handle module 400 may power an augmented ophthalmoscope module 500 or an augmented otoscope module 450.

In step 1022, controller 402 of augmented handle module 400 initializes at least one sensor 404. For example, controller 402 may initialize a set of parameters and/or thresholds for the at least one sensors 404, e.g., based on a predetermined program for assessing the student.

In step 1024, controller 402 of augmented handle module 400 senses/reads the at least one sensor 404. For example, controller 402 may sense the at least one sensor 404 by receiving examination data from the at least one sensor 404. Additionally or alternatively, augmented handle module 400 may read/sense the sensor(s) of an augmented ophthalmoscope module 500 or an augmented otoscope module 450.

In step 1026, controller 402 of augmented handle module 400 checks at least one threshold. Controller 402 may check a threshold by comparing the data received from the at least one sensor 404 to a predetermined threshold, such as a threshold initialized in step 1022. Augmented handle module 400 may trigger augmented functionalities, such as modulate visual content 472, based on a threshold being satisfied or not satisfied.

In step 1028, memory storage 406 stores data received from the at least one sensor 404. Although FIG. 4 illustrates memory storage 406 as located within augmented handle module 400, in one embodiment memory storage 406 is located externally from augmented handle module 400, such as in an external device, in augmented ophthalmoscope module 500 and/or in augmented otoscope module 450.

In step 1030, augmented handle module 400 streams the data received from the at least one sensor 404, e.g., to control module 104. The data may be streamed by way of communication element 410. Steps 1024 to 1030 may be repeated iteratively throughout a student's use of the augmented device.

In step 1032, visual content is modulated to perform augmented functionalities. Although step 1032 is depicted as modulating the visual content in the embodiment illustrated in FIG. 10, the visual content may be modified, replaced, blended, and/or overlaid as discussed herein. Augmented handle module 400 may provide augmented functionalities by generating simulated physical parameters corresponding to or based on augmented data, which may be presented as information/content by overlaying examination data with prerecorded signals. Augmented handle module 400 may include a presentation device, such as a display or speaker, to present the simulated physical parameters as visual content and/or audio content. In the embodiment illustrated in FIG. 10, the visual content is modulated based on data received from augmented handle module 400 and one of augmented ophthalmoscope module 500 or augmented otoscope module 450. For example, augmented handle module 400 may trigger augmented functionalities that overlay visual content on the video displayed to the student based on a threshold being satisfied. In one embodiment, when a threshold comparing the sensed examination data to a predetermined proximity or distance value of the augmented handle 400 to the object (e.g., patient) is satisfied, the augmented handle module 400 triggers the overlay/modulation of visual content to display simulated physical parameters as content to the student regarding the use of the augmented ophthalmoscope module 500 or augmented otoscope module 450. Additionally and/or alternatively, augmented ophthalmoscope module 500 or augmented otoscope module 450 may stream the tracked video or image.

Figure 11:
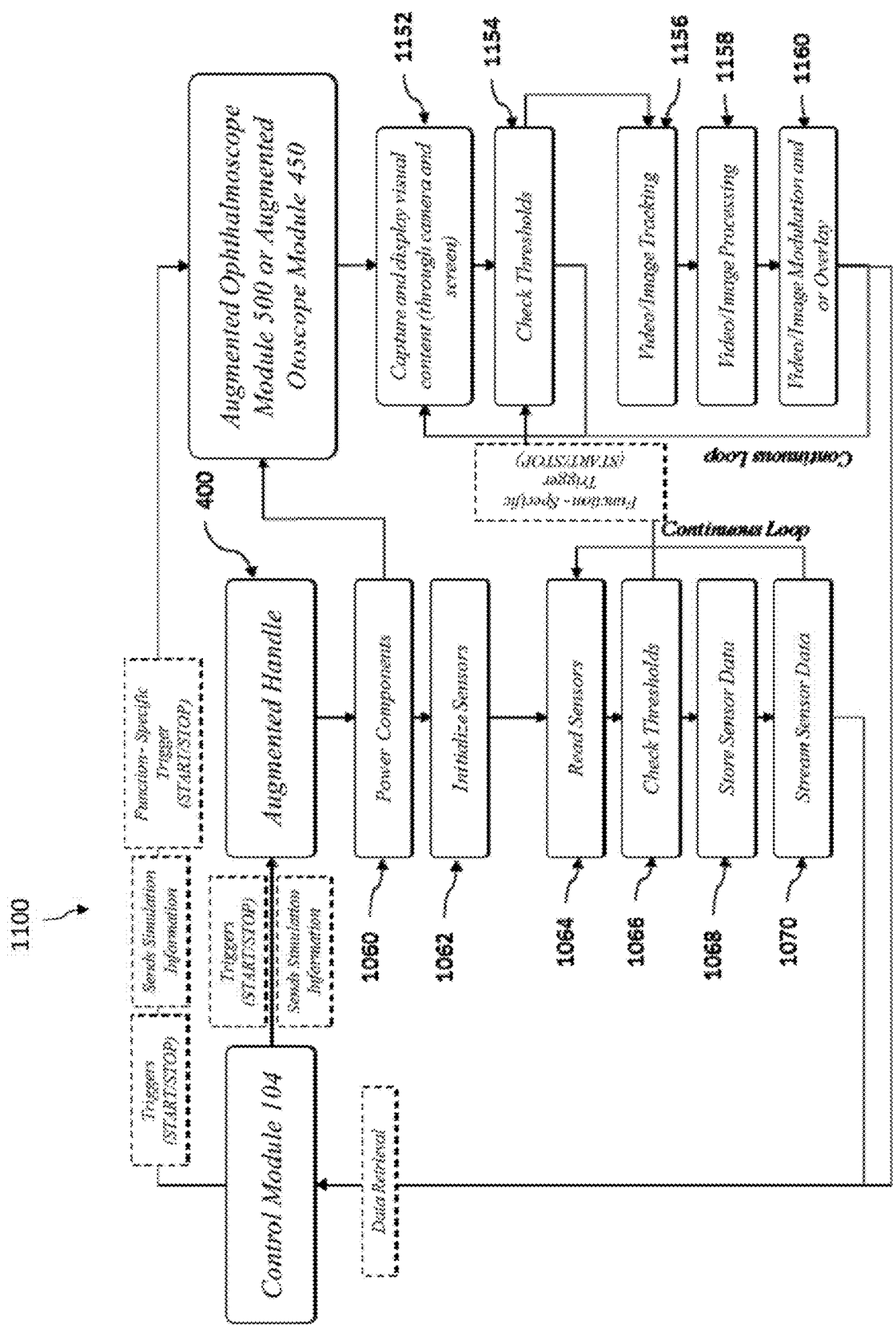
FIG. 11 is a schematic depicting a flowchart for utilizing an augmented ophthalmoscope module or an augmented otoscope module for assessing a student in accordance with aspects of the invention.

FIG. 11 is a schematic depicting a flowchart 1100 for utilizing an augmented ophthalmoscope module 500 or an augmented otoscope module 450 for assessing a student in accordance with aspects of the invention.

Flowchart 1100 includes utilizing an augmented handle module 400 in accordance with the steps of flowchart 900. Additionally, flowchart 1100 includes the steps of capturing and displaying visual content 1152; checking thresholds 1154; image tracking 1156; image processing 1158; and image modulation and/or overlay 1160.

In step 1152, augmented ophthalmoscope module 500 or augmented otoscope module 450 captures and/or displays visual content using at least one image sensor. Suitable image sensors include charge coupled devices, complementary metal-oxide-semiconductors, or other filmless camera sensors. The image sensor(s) may be configured for video and/or image recording.

In step 1154, augmented ophthalmoscope module 500 or augmented otoscope module 450 checks at least one threshold. Augmented ophthalmoscope module 500 or augmented otoscope module 450 may check a threshold by comparing the examination data received from the at least one sensor to a predetermined threshold, such as a threshold initialized in step 1152. Additionally or alternatively, augmented ophthalmoscope module 500 or augmented otoscope module 450 may receive a function specific trigger from augmented handle module 400 that triggers augmented functionalities when the function specific trigger satisfies or does not satisfy a certain threshold. Augmented ophthalmoscope module 500 or augmented otoscope module 450 may trigger augmented functionalities, such as modulate visual content 1160, based on a threshold being satisfied or not satisfied.

In step 1156, augmented ophthalmoscope module 500 or augmented otoscope module 450 tracks the video or image obtained in step 1152. For example, the augmented ophthalmoscope module 500 or augmented otoscope module 450 may be configured to identify one or more features of the patient (e.g., the patient's pupil and/or iris). As augmented ophthalmoscope module 500 or augmented otoscope module 450 is moved or displaced relative to the patient, the augmented ophthalmoscope module 500 or augmented otoscope module 450 may be configured to track the identified features of the patient. Augmented ophthalmoscope module 500 or augmented otoscope module 450 may be configured to use color and/or texture characteristics to track features of the patient-such as the color of the patient's retina, iris, and/or pupil—and to trigger augmented functionalities.

In step 1158, augmented ophthalmoscope module 500 or augmented otoscope module 450 processes the video or image. Augmented ophthalmoscope module 500 or augmented otoscope module 450 may process the video or image obtained in step 1152 using a processor to produce examination data corresponding to the images or video obtained by the at least one image sensor. Augmented ophthalmoscope module 500 or augmented otoscope module 450 may have one or more processors dedicated to feature recognition and tracking based on the data received relating to the obtained video or images. For example, augmented ophthalmoscope module 500 may track a video or image of features of a patient's eye (e.g., the patient's pupil and/or iris) and/or use one or more processors to determine a change in the distance of augmented ophthalmoscope module 500 from the patient's eye. In one embodiment, a change in the distance of augmented ophthalmoscope module 500 from the patient's eye is determined based on the size of the tracked features of the patient's eye increasing or decreasing in the field of view of the video or images obtained in step 1152.

In step 1160, augmented ophthalmoscope module 500 or augmented otoscope module 450 modulates and/or overlays the images or video obtained from step 1156. The augmented functionalities may be triggered by the examination data satisfying a threshold as in step 1154. The examination data may be produced by the sensor or processor based on the image or video obtained in step 1152. In one embodiment, as the augmented ophthalmoscope module 500 approaches the eye, features of the patient's eye (e.g., the patient's pupil and/or iris) becomes larger with respect to the field of view for the videos or images of the patient's eye, which may satisfy a threshold that triggers augmented functionalities.

Augmented ophthalmoscope module 500 or augmented otoscope module 450 may modulate and/or overlay the images or videos obtained in step 1152 to provide augmented functionalities. For example, ophthalmoscope module 500 or augmented otoscope module 450 may identify features of the patient, track the features of the patient, and produce at least one simulated physical parameter based on augmented data for presentment to the student as content (e.g., visual content, such as images or video). The images corresponding to the simulated physical parameters may be produced by overlaying (e.g., superimposing) prerecorded content/information (e.g., images) onto at least portions of the image or video obtained by the sensors. Alternatively and/or additionally, the images corresponding to the simulated physical parameters may be produced by modulating or modifying the image or video obtained by the sensors. In one embodiment, video or image data is processed to manipulate or overlay the examination for enhancing the content presented to the student. In another embodiment, the augmented functionalities may be modify the color of the displayed image and/or blur the displayed visual content (e.g. an image).

Additionally and/or alternatively, the augmented functionalities of augmented ophthalmoscope module 500 or augmented otoscope module 450 may be triggered by communication with other augmented modules or devices, such as augmented handle module 400. For example, augmented ophthalmoscope module 500 or augmented otoscope module 450 may communicate with additional augmented handle module 400 and/or control module 104 to stream, store, manipulate input examination data, and generate output augmented data and/or simulated physical parameters that are presented as video/image information/content.

Figure 12:
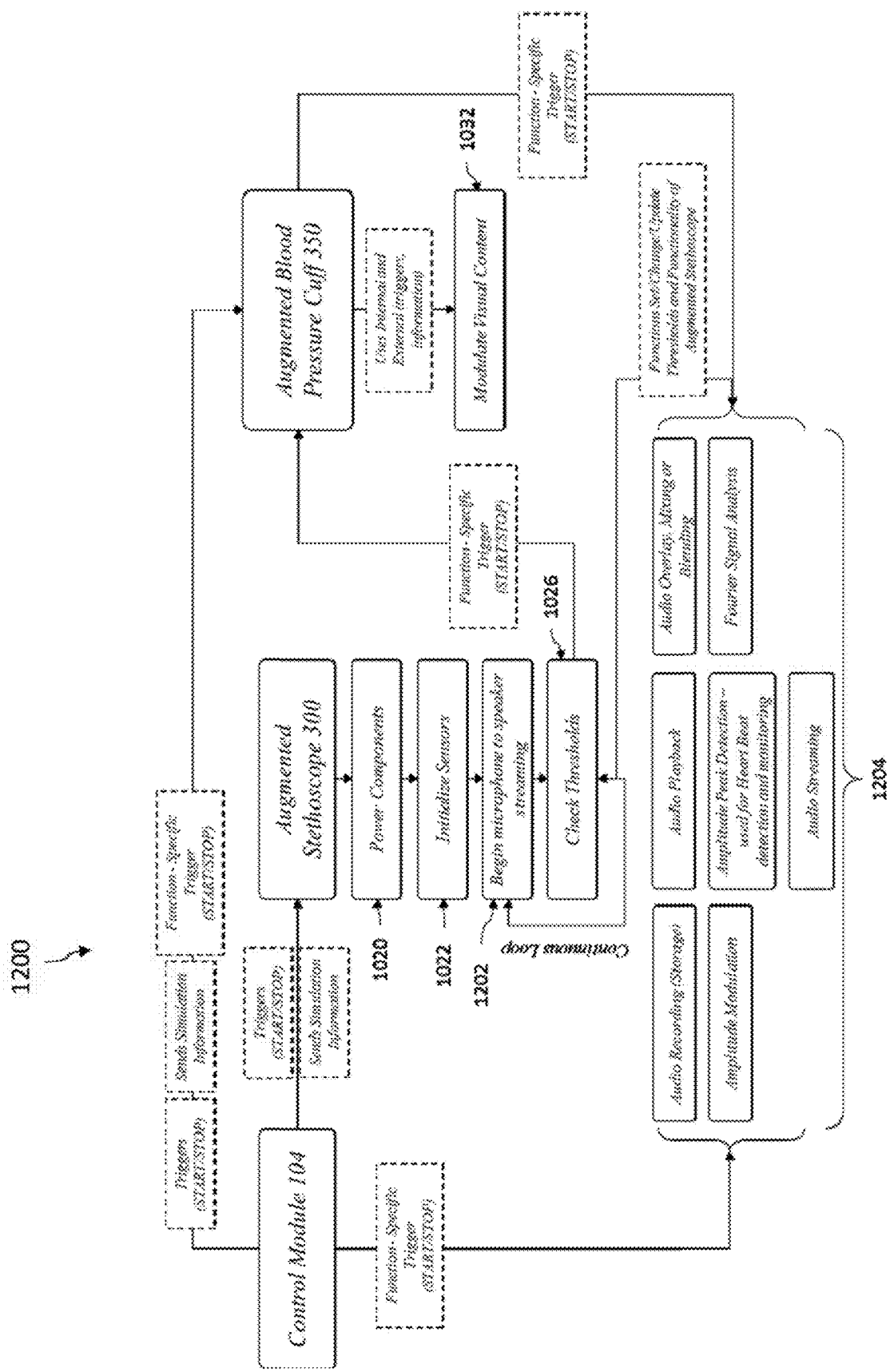
FIG. 12 is a first schematic depicting a flowchart for utilizing an augmented stethoscope module and augmented blood pressure module for assessing a student according to aspects of the invention.

FIG. 12 is a first schematic depicting a flowchart 1200 for utilizing an augmented stethoscope module 300 and augmented blood pressure module 350 for assessing a student in accordance with aspects of the invention.

Flowchart 1200 includes utilizing an augmented stethoscope 300 for the steps of powering at least one component 1020, initializing at least one sensor 1022, streaming microphone to at least one speaker, checking at least one threshold 1026 and utilizing an augmented blood pressure module 350 for modulating visual content 472 and performing additional augmented functionalities 1204.

In step 1202, augmented stethoscope module 300 initiates streaming of a microphone to at least one speaker. The augmented stethoscope module 300 may include an acoustic transducer to convert the input audio into an analog or digital signal. In one embodiment, the augmented stethoscope module includes a dedicated array of processors that converts analog signals in to digital signals for streaming, storing, and/or manipulation. Augmented stethoscope module 300 may also have electroacoustic transducers to stream input audio and/or recorded signals. Augmented stethoscope module 300 may have on-board volatile and non-volatile memory for short and/or long-term data storage.

In step 1204, augmented stethoscope module 300 and/or augmented blood pressure module 350 implements additional steps for performing augmented functionalities. Additional steps for performing augmented functionalities includes audio recording/storage, amplitude modulation, audio playback, amplitude detection used for heart beat detection and monitoring, audio streaming, audio overlay, mixing of blending, Fourier signal analysis, and frequency-base signal analysis. For example, augmented stethoscope module 300 and/or augmented blood pressure 350 may be configured to record and stream audio content (e.g., audio of the patient's heart beat) using at least one microphone and/or acoustic transducer. The audio content/examination data may be analyzed using one or more processors to determine a pattern, e.g., a pattern associated with the amplitude of a heartbeat and/or the frequency of the heartbeat. The audio content corresponding to examination data received from the patient may be overlaid, mixed, blended, and/or replaced with the prerecorded audio content corresponding with augmented data to generate simulated physical parameters, which may be presented to the student as simulated content (e.g., audio content).

In one embodiment, the simulated physical parameters corresponding to the audio content may be generated by superposing pre-recorded heart or lung sounds onto the input heart or lung sounds associated with the examination data. In another embodiment, the simulated physical parameters corresponding to the audio content may be generated by modifying input heart or lung sounds, amplify or attenuate the input heart or lung sounds, fade the signal of the input heart or lung sounds, etc. Additionally and/or alternatively, augmented stethoscope module 300 may use proximity sensors or magnetic tracking sensors, either on the stethoscope or blood pressure cuff, to trigger augmentation functionalities.

A student may utilize the augmented stethoscope module 300 and augmented blood pressure module 350 by pumping the cuff pressure to provide an applied pressure to the patient's arm, such that the student is able to hear audio sounds of the patient's heartbeat. The student may measure through the augmented stethoscope module 300 and/or augmented blood pressure module 350 the applied pressure every 0.1 seconds. The applied pressure may be displayed on the control base LCSD screen. The stethoscope module 300 may measure and record the live audio sounds from the patient during use by the student. The augmented stethoscope module 300 and/or augmented blood pressure 350 is configured to present an output signal including the examination data (e.g., in a real-time mode) and/or an output signal including at least one simulated physical parameter (e.g. In an augmented mode).

In the real-time mode, the system (e.g., augmented stethoscope module 300, augmented blood pressure 350, and/or control module 104) may present audio sounds of the patient's heartbeat, such that the student hears the actual Korotkoff sounds of the patient. In the augmented mode, the stethoscope may be placed on the patient (correct placement may be recorded), pressure cuff is inflated, the pressures are recorded, the patient sounds are recorded but the synthetic audio sounds are generated, e.g., by overlaying the live audio sounds so that the student hears the appropriate sounds at the appropriate displayed pressures to indicate and mimic the augmented blood pressure. The simulated physical parameters corresponding to the audio content may be generated by overlaying, replacing, and/or blending augmented data or prerecorded media with the examination data/media sensed by the sensors.

For example, in the augmented mode, the student hears live sounds from augmented stethoscope 300. When placed on the chest of the patient, the system (e.g., augmented stethoscope 300 and/or control module 104) examines/determines if it hears audio sounds associated with the patient's heart and/or lungs, determines the amplitude of the heart/lung sounds and then blends, overlays, and/or replaces the heart/lung sounds with synthetic or prerecorded sounds. The live environmental backgrounds sounds may still be transmitted in real-time and blended with prerecorded sounds or augmented data thereof to make the simulation realistic. Accordingly, the system may be configured to hear, record, and analyze the heart sounds; calculate the heart rate; and present/play a blended audio signal to the student using a presentation device. The blended audio signal may be modified in real-time. In one embodiment, if the student moves the stethoscope on the patient's skin surface the student hears the movement. In another embodiment, if the student moves the stethoscope on the skin surface but away from the heart, the measured amplitude of the heart beat is reduced so the synthesized heart sounds heard by the student are reduced in amplitude. If the heart beat sounds reduce to below a threshold (e.g., below an audible level by humans), the system will modify the blended audio signal to also remove heart sounds.

Figure 13:
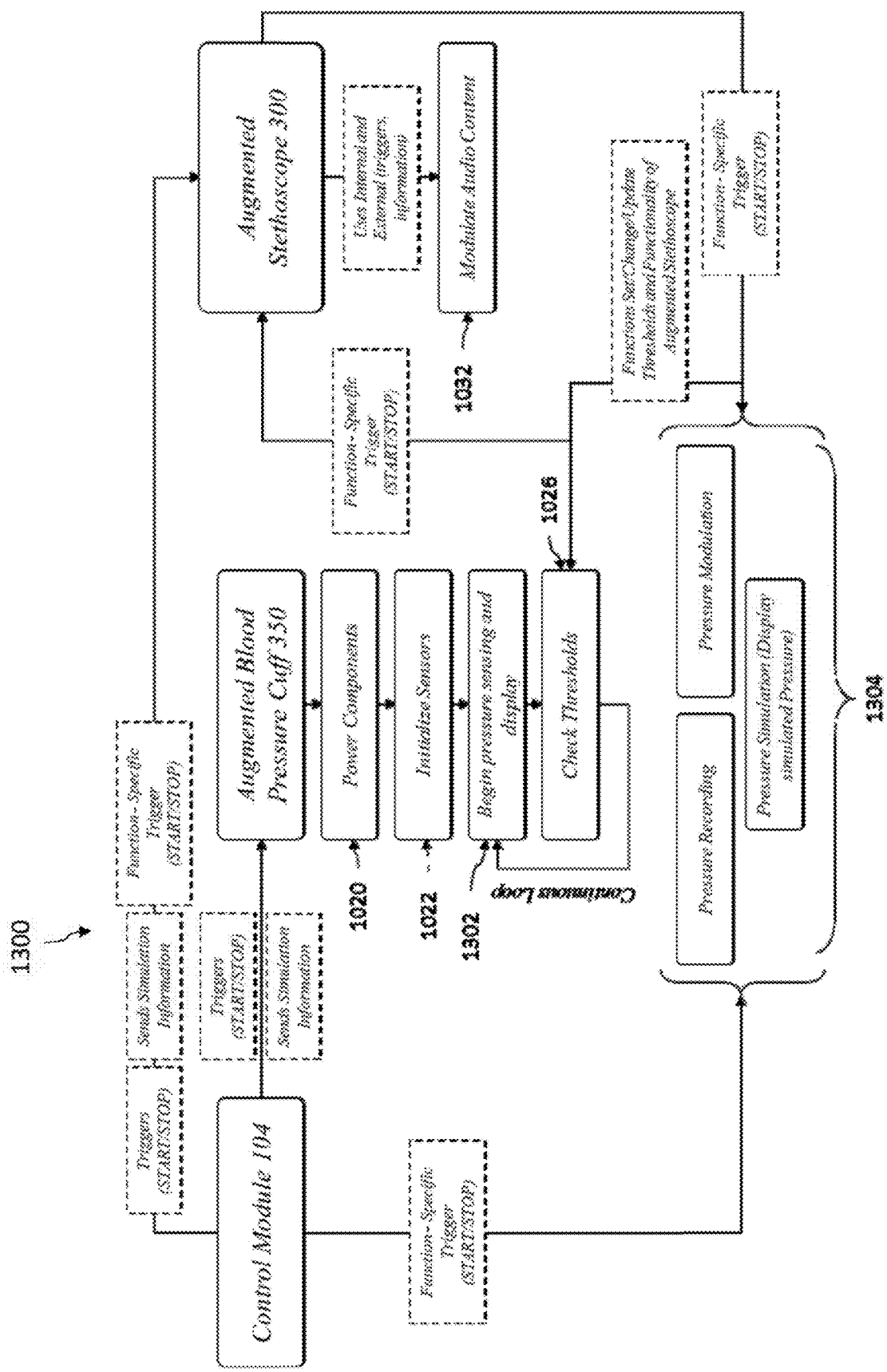
FIG. 13 is a second schematic depicting a flowchart for utilizing an augmented stethoscope module and augmented blood pressure module for assessing a student in accordance with aspects of the invention.

FIG. 13 is a second schematic depicting a flowchart 1300 for utilizing an augmented stethoscope module 300 and augmented blood pressure module 350 for assessing a student in accordance with aspects of the invention.

Flowchart 1300 includes utilizing an augmented blood pressure module 350 for the steps of powering at least one component 1020, initializing at least one sensor 1022, sensing and displaying blood pressure 1302, checking the threshold(s) 1026, and utilizing an augmented stethoscope 300 for modulating visual content 472 and additional augmented functionalities 1304.

In step 1302, augmented blood pressure module 350 initiates sensing and/or displaying of the patient's blood pressure. Augmented blood pressure module 350 includes at least one sensor 358 configured to sense a patient's blood pressure. Augmented blood pressure module 350 may also include a pressure transducer that converts pressure into examination data, e.g., in the form of an analog or digital signal. Augmented blood pressure module 350 may also include a dedicated array of processors for analyzing the blood pressure sensed by sensor 358 and/or converting analog signals into digital signals for streaming, storing, and/or manipulation.

In step 1304, augmented stethoscope module 300 and/or augmented blood pressure module 350 implements additional steps for performing augmented functionalities. Additional steps for performing augmented functionalities includes pressure recording, pressure modulation, and pressure simulation/display of a simulated physical parameters corresponding to pressure. For example, augmented blood pressure module 350 may be configured to use at least one processor to modulate inputted examination pressure data and display simulated physical parameters. In one embodiment, augmented functionalities are triggered by a pressure sensor sensing an applied pressure that satisfies a threshold. For example, augmented blood pressure module 350 may measure a real pressure in the cuff, using a pressure sensor, and compares the value to a threshold value stored in memory or sent by another device.

Figure 14:
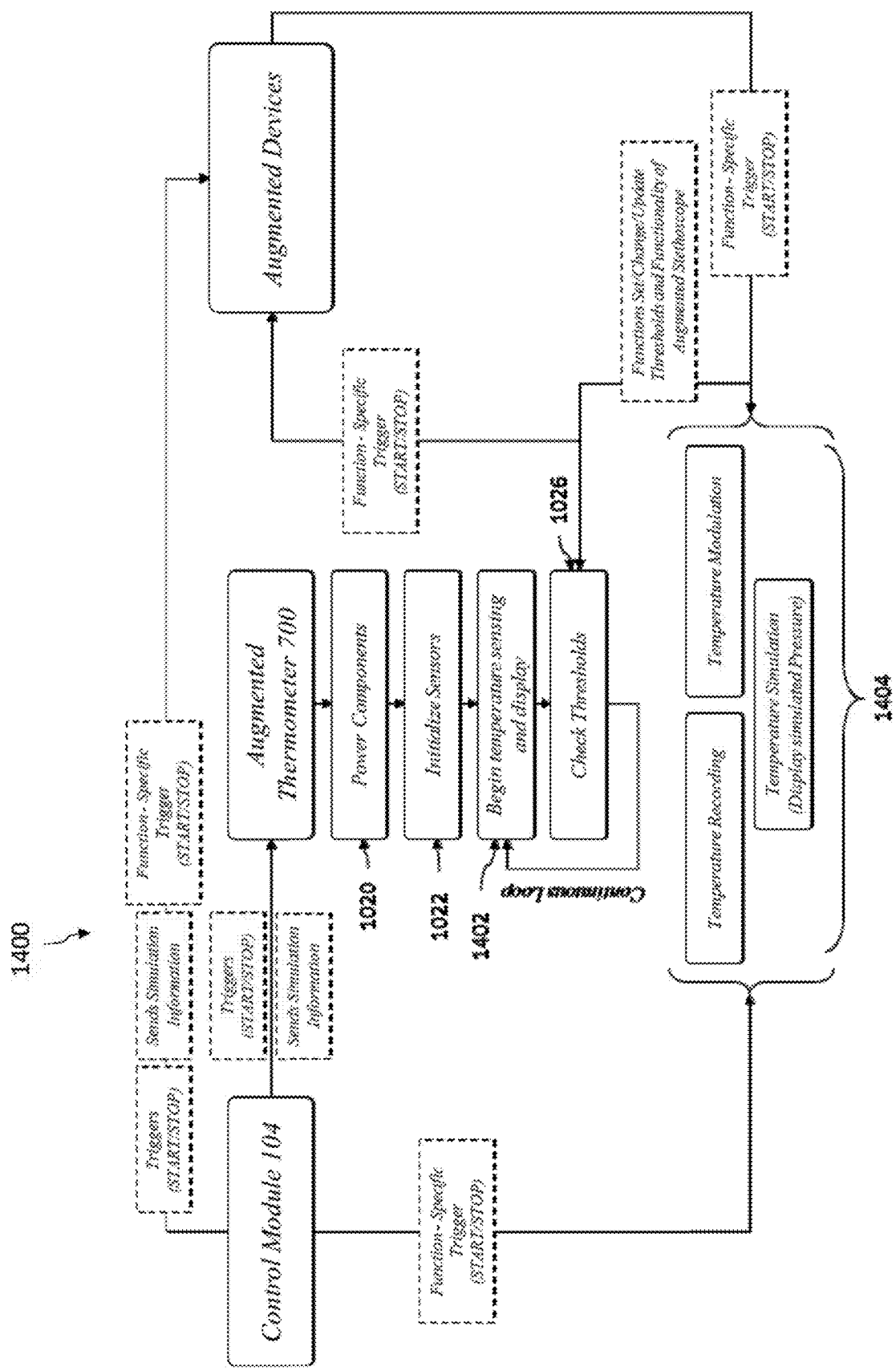
FIG. 14 is a schematic depicting a flowchart for utilizing an augmented thermometer for assessing a student according to aspects of the invention.

FIG. 14 is a schematic depicting a flowchart 1400 for utilizing an augmented thermometer for assessing a student in accordance with aspects of the invention.

Flowchart 1400 includes utilizing an augmented thermometer 700 for the steps of powering at least one component 1020, initializing at least one sensor 1022, sensing and displaying temperature(s) 1402, checking the threshold(s) 1026, and performing additional augmented functionalities 1404.

In step 1402, augmented thermometer 700 senses and/or displays a temperature of the patient. Augmented thermometer 700 includes at least one sensor 710 configured to sense a patient's blood pressure. Augmented thermometer 700 may include a pressure transducer that converts pressure into examination data, e.g., in the form of an analog or digital signal. Augmented thermometer 700 may also include a dedicated array of processors for analyzing the sensed temperature and/or converting analog signals into digital signals for streaming, storing, and/or manipulation.

In step 1404, augmented thermometer 700 implements additional steps for performing augmented functionalities. Additional steps for performing augmented functionalities includes recording the examination data for a sensed temperature, temperature modulation, and simulation of temperature/display of a simulated physical parameter associated with temperature. For example, augmented thermometer 700 may be configured to use at least one processor to modulate inputted examination temperature data and display simulated physical parameter based on augmented data, such as simulated temperature values. The augmented thermometer 700 may communicate with one or more augmented devices to enable one or more augmented functionalities.

Figure 15:
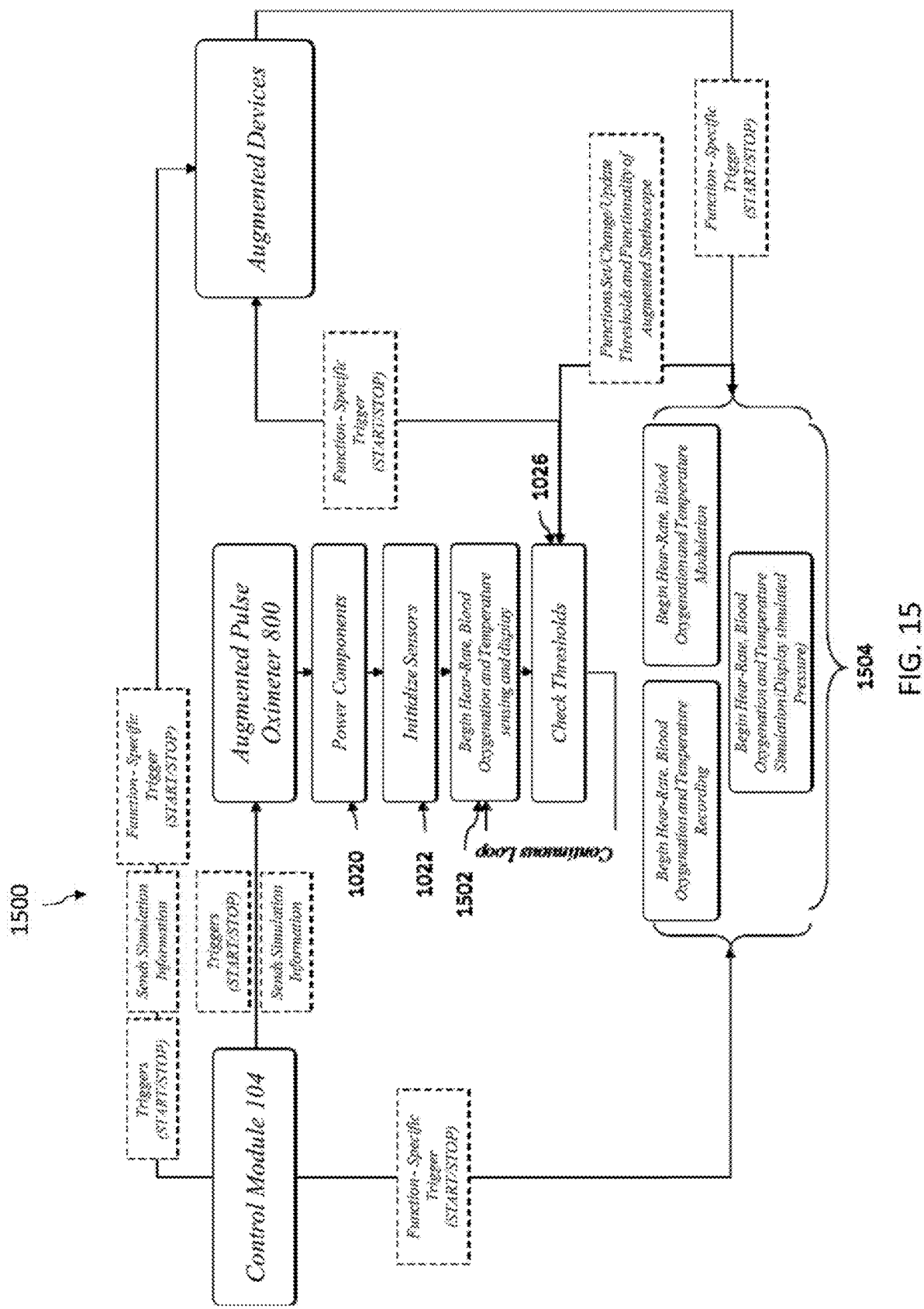
FIG. 15 is a schematic depicting a flowchart for utilizing an augmented pulse oximeter for assessing a student in accordance with aspects of the invention.

FIG. 15 is a schematic depicting a flowchart 1500 for utilizing an augmented pulse oximeter for assessing a student in accordance with aspects of the invention.

Flowchart 1500 includes utilizing an augmented pulse oximeter 800 for the steps of powering at least one component 1020, initializing at least one sensor 1062, sensing and displaying a patient's heartrate, blood oxygenation, and/or temperature 1502, checking at least one threshold 1026, and performing additional augmented functionalities 1504. The at least one sensor 4652 may sense the presence of a fingertip using an on-board IR sensor.

In step 1502, augmented pulse oximeter 800 senses and/or displays a patient's heartrate, blood oxygenation, and/or temperature. Augmented pulse oximeter 800 includes at least one sensor 810 configured to sense a patient's blood pressure. Augmented pulse oximeter 800 may include a transducer that converts sensed heartrates, blood oxygenation, and/or temperature into examination data, e.g., in the form of an analog or digital signal. Augmented pulse oximeter 800 may also include a dedicated array of processors for analyzing the sensed physiological parameters and/or converting analog signals into digital signals for streaming, storing, and/or manipulation.

In step 1504, augmented pulse oximeter 800 implements additional steps for performing augmented functionalities. Additional steps for performing augmented functionalities include recording a heartrate, blood oxygenation, and/or temperature; modulation of a heartrate, blood oxygenation, and/or temperature; and simulation and/or display of a heartrate, blood oxygenation, and/or temperature. For example, augmented pulse oximeter 800 may be configured to use at least one processor to modulate sensed heartrate, blood oxygenation, and/or temperature and display simulated physical parameter, such as physiological parameters.

The simulated physical parameters based on augmented data may be generated by overlaying (e.g., superimposing) prerecorded content/data (e.g., images, values, patterns physiological parameters) onto at least portions of the examination data corresponding to the sensed heartrate, blood oxygenation, and/or temperature. Alternatively and/or additionally, the simulated physical parameters may be produced by modulating or modifying the examination data sensed by the augmented pulse oximeter 800. In one embodiment, augmented pulse oximeter 800, upon triggering the augmentation, superposes and/or modifies a prerecorded heart rate or oxygenation values onto the real measurements corresponding to the examination data. The superposed values are then presented to the student through a display. In another embodiment, upon triggering the augmentation, augmented pulse oximeter 800 modifies or modulated the sensed examination data associated with the sensed physiological parameters to generate simulated physical parameters/augmented data that represent truncated/reduced or increased physical parameters (e.g., an increased peak heart rate).

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An apparatus comprising:
   at least one sensor configured to sense at least one physical parameter during examination of a subject by a student; and
   a processor configured to
      receive the at least one sensed physical parameter,
      produce examination data that corresponds to the at least one sensed physical parameters,
      present at least one of an output signal including the examination data or an output signal including augmented data,
      wherein the processor is configured to generate at least one simulated physical parameter based on the augmented data, and
      wherein the at least one simulated physical parameter corresponds to an amplification or reduction of the sensed one or more physiological parameters.

2. The apparatus of claim 1, wherein the processor is configured to compare the examination data to a threshold.

3. The apparatus of claim 2, wherein the processor is configured to produce and present the at least one simulated physical parameter upon the threshold being satisfied and present examination data when the threshold is not satisfied.

4. A method, the method comprising:
- sensing one or more physical parameters with an augmented medical instrument during examination of a subject by a student;
- producing an output signal with a processor, the output signal including examination data corresponding to the one or more sensed physical parameters;
- presenting at least one simulated physical parameter as content to the student; and
- generating the at least one simulated physical parameter based on the augmented data,
- wherein the one or more simulated physical parameters is generated by modulating the examination data with the augmented data.

5. The method of claim 4, wherein the one or more simulated physical parameters is generated by overlaying the examination data with the augmented data.

6. The method of claim 4, wherein the one or more simulated physical parameters is generated by replacing the examination data with the augmented data.

7. The method of claim 4, further comprising generating the at least one simulated physical parameter by modifying the examination data.

8. The method of claim 4, wherein the content presented to the student is at least one of audio content or visual content.

9. The method of claim 4, further comprising comparing the examination data to standardized data and assessing the student based on the comparison.

10. A system comprising:
- a first augmented medical instrument configured to sense a first physical parameter during examination of a subject and produce a first examination data;
- a second augmented medical instrument configured to sense a second physical parameter during examination of the subject and produce a second examination data;
- wherein the system is configured to generate at least one simulated physical parameter based on the first examination data and present the at least one simulated physical parameter to the student on the second augmented medical instrument.

11. The system of claim 10, wherein the at least one simulated physical parameter includes at least one of the first examination data and the second examination data overlaid with augmented data.

12. The system of claim 10, wherein the at least one simulated physical parameter includes at least one of the first examination data and the second examination data replaced with augmented data.

13. The system of claim 10, wherein the at least one simulated physical parameter includes at least one of the first examination data and the second examination data modified with augmented data.

14. The system of claim 10, wherein the at least one simulated physical parameter includes at least one of the first examination data and the second examination data modulated with augmented data.

15. The system of claim 10, wherein the simulated physical parameter corresponds to audio content presented as a sound of a heart murmur.

16. The system of claim 10, wherein at least one of the first augmented medical instrument and the second augmented medial instrument is an ophthalmoscope, otoscope, thermometer, stethoscope, pulse oximeter, or an blood pressure module.

17. The system of claim 10, further comprising a base system that includes a panel module and an augmented instrument receptacle panel coupled to the panel module, the augmented instrument receptacle panel configured to receive at least one of the first augmented medical instrument and the second augmented medical instrument.

18. The system of claim 17, wherein the base system is configured to compare the examination data to standardized data, and generate a report based on the comparison.

* * * * *